US012697490B2

(12) United States Patent
Ridler et al.

(10) Patent No.: US 12,697,490 B2
(45) Date of Patent: Aug. 4, 2026

(54) HYBRID MULTI-PHASIC STIMULATION

(71) Applicant: Cochlear Limited, Macquarie University (AU)

(72) Inventors: Oliver John Ridler, Cherrybrook (AU); Zachary Mark Smith, Pymble (AU); Brett Anthony Swanson, St. Ives (AU)

(73) Assignee: Cochlear Limited, Macquarie University (AU)

( * ) Notice: Subject to any disclaimer, the term of this patent is extended or adjusted under 35 U.S.C. 154(b) by 502 days.

(21) Appl. No.: 17/922,876

(22) PCT Filed: Mar. 30, 2021

(86) PCT No.: PCT/IB2021/052633
§ 371 (c)(1),
(2) Date: Nov. 2, 2022

(87) PCT Pub. No.: WO2021/229316
PCT Pub. Date: Nov. 18, 2021

(65) Prior Publication Data
US 2023/0158299 A1    May 25, 2023

Related U.S. Application Data

(60) Provisional application No. 63/022,810, filed on May 11, 2020.

(51) Int. Cl.
*A61N 1/36* (2006.01)
*A61N 1/372* (2006.01)
(52) U.S. Cl.
CPC ......... *A61N 1/36038* (2017.08); *A61N 1/372* (2013.01)

(58) Field of Classification Search
CPC .............................. A61N 1/37; A61N 1/36125
See application file for complete search history.

(56) References Cited

U.S. PATENT DOCUMENTS

| | | | |
|---|---|---|---|
| 4,408,608 A | 10/1983 | Daly et al. | |
| 5,107,834 A * | 4/1992 | Ideker .................. | A61N 1/3918 607/5 |
| 5,776,172 A | 7/1998 | Schulman et al. | |

(Continued)

FOREIGN PATENT DOCUMENTS

WO        02-082982 A1    10/2002

OTHER PUBLICATIONS

International Search Report and Written Opinion in counterpart International Application No. PCT/IB2021/052633, mailed Jul. 7, 2021, 8 pages.

(Continued)

*Primary Examiner* — Eric D. Bertram
(74) *Attorney, Agent, or Firm* — Edell, Shapiro & Finnan, LLC

(57) ABSTRACT

Presented herein are hybrid multi-phasic stimulation techniques for stimulation of tissue of a recipient of an implantable medical device. In particular, in accordance with the hybrid multi-phasic stimulation techniques, at least one stimulation current pulse is delivered to the tissue of the recipient in order to stimulate the tissue. The at least one stimulation current pulse injects charge into the tissue that is then removed through the combination of at least one discharging current pulse and a period of electrode shorting.

19 Claims, 18 Drawing Sheets

(56) References Cited

U.S. PATENT DOCUMENTS

| | | | |
|---|---|---|---|
| 6,035,237 | A | 3/2000 | Schulman et al. |
| 8,454,529 | B2 * | 6/2013 | Daly .................. A61N 1/36038 |
| | | | 607/30 |
| 8,494,626 | B2 | 7/2013 | Moffitt et al. |
| 8,867,763 | B2 | 10/2014 | Bouse |
| 8,989,413 | B2 | 3/2015 | Ridler et al. |
| 9,124,990 | B2 | 9/2015 | Strelcyk et al. |
| 9,375,575 | B2 | 6/2016 | Moffitt et al. |
| 9,596,551 | B2 | 3/2017 | Pedersen et al. |
| 9,641,942 | B2 | 5/2017 | Strelcyk et al. |
| 9,795,795 | B2 | 10/2017 | Seligman et al. |
| 9,886,954 | B1 | 2/2018 | Meacham et al. |
| 9,956,406 | B2 | 5/2018 | Long et al. |
| 10,051,387 | B2 | 8/2018 | Udesen et al. |
| 10,117,032 | B2 | 10/2018 | Gordon et al. |
| 10,142,744 | B2 | 11/2018 | Mauler |
| 10,536,783 | B2 | 1/2020 | Sanger et al. |
| 2005/0101878 | A1 * | 5/2005 | Daly .................. A61N 1/36038 |
| | | | 600/554 |
| 2007/0225767 | A1 * | 9/2007 | Daly .................. A61N 1/36038 |
| | | | 607/2 |
| 2008/0114405 | A1 * | 5/2008 | Palmer .................... A61N 1/37 |
| | | | 607/2 |
| 2009/0118795 | A1 | 5/2009 | Ibrahim et al. |
| 2018/0015286 | A1 | 1/2018 | Liedler et al. |
| 2019/0329041 | A1 * | 10/2019 | Corndorf .......... A61N 1/36125 |
| 2019/0342676 | A1 | 11/2019 | Wurzbacher et al. |
| 2020/0360693 | A1 * | 11/2020 | Scheltienne ....... A61N 1/36062 |

OTHER PUBLICATIONS

Carlyon, Robert P. et al., "Effect of stimulus polarity on detection thresholds in cochlear implant users: relationships with average threshold, gap detection, and rate discrimination," Journal of the Association for Research in Otolaryngology, doi: https://doi.org/10. 1101/297085, Apr. 7, 2018, 30 pages.

McKay, Colette M., "The perceptual effects of interphase gap duration in cochlear implant stimulation," Hearing Research 181 (2003) 94-99, May 7, 2023, 6 pages.

* cited by examiner

*FIG. 3*

349
MONOPHASIC
STIMULATION SIGNAL

354
SHORTING

CATHODIC
PULSE

350

TIME

Figure 11:
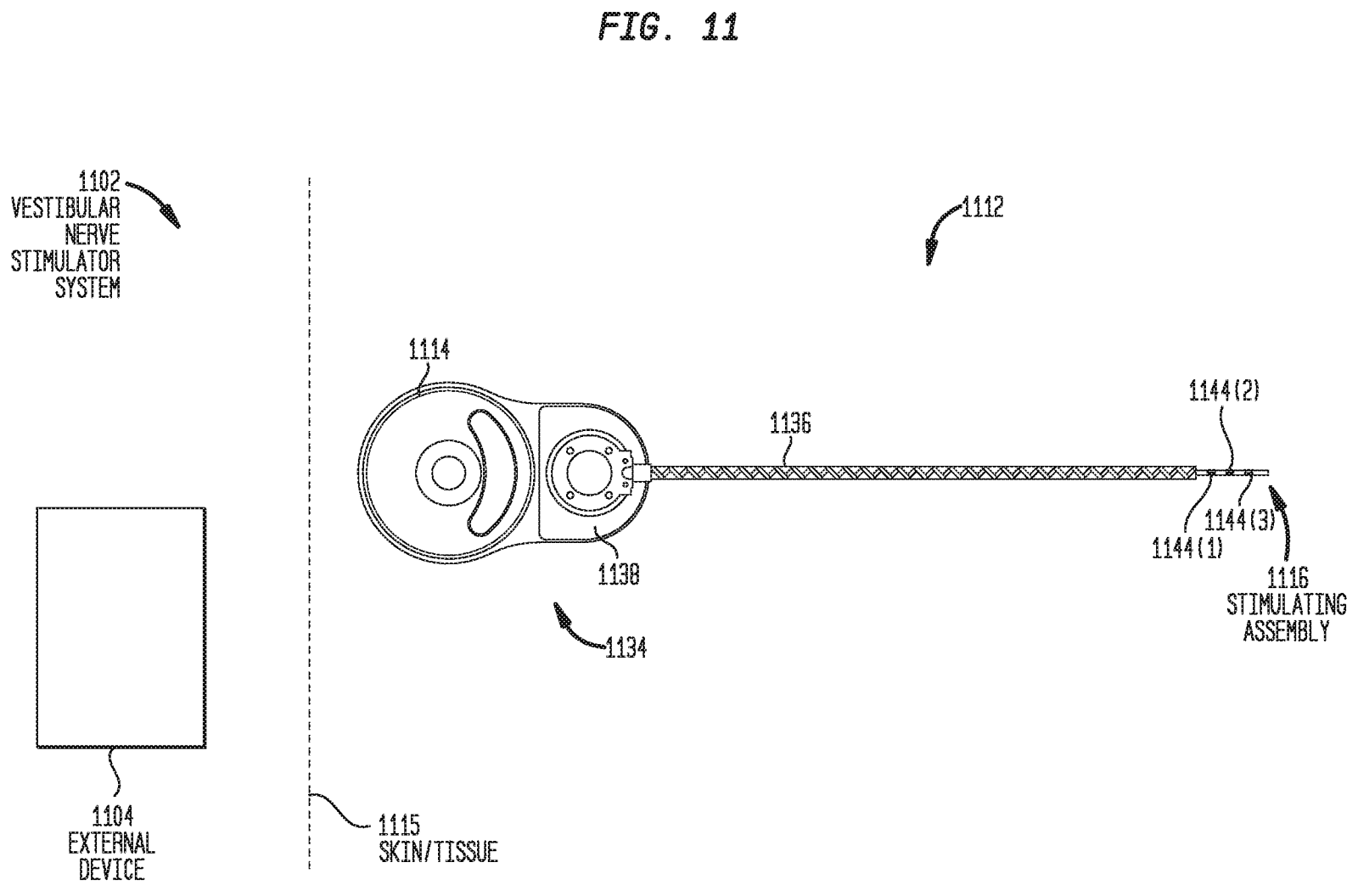

1116
STIMULATING
ASSEMBLY

1136

1138

1134

1114

1115
SKIN/TISSUE

1102
VESTIBULAR
NERVE
STIMULATOR
SYSTEM

1104
EXTERNAL
DEVICE

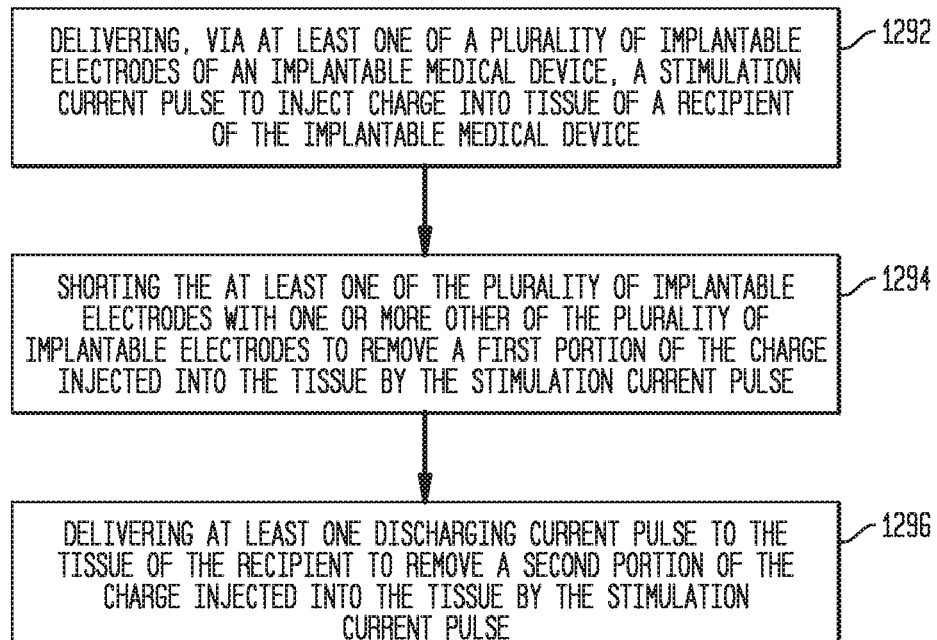

DELIVERING, VIA AT LEAST ONE OF A PLURALITY OF IMPLANTABLE ELECTRODES OF AN IMPLANTABLE MEDICAL DEVICE, A STIMULATION CURRENT PULSE TO INJECT CHARGE INTO TISSUE OF A RECIPIENT OF THE IMPLANTABLE MEDICAL DEVICE — 1292

SHORTING THE AT LEAST ONE OF THE PLURALITY OF IMPLANTABLE ELECTRODES WITH ONE OR MORE OTHER OF THE PLURALITY OF IMPLANTABLE ELECTRODES TO REMOVE A FIRST PORTION OF THE CHARGE INJECTED INTO THE TISSUE BY THE STIMULATION CURRENT PULSE — 1294

DELIVERING AT LEAST ONE DISCHARGING CURRENT PULSE TO THE TISSUE OF THE RECIPIENT TO REMOVE A SECOND PORTION OF THE CHARGE INJECTED INTO THE TISSUE BY THE STIMULATION CURRENT PULSE — 1296

Figure 14:
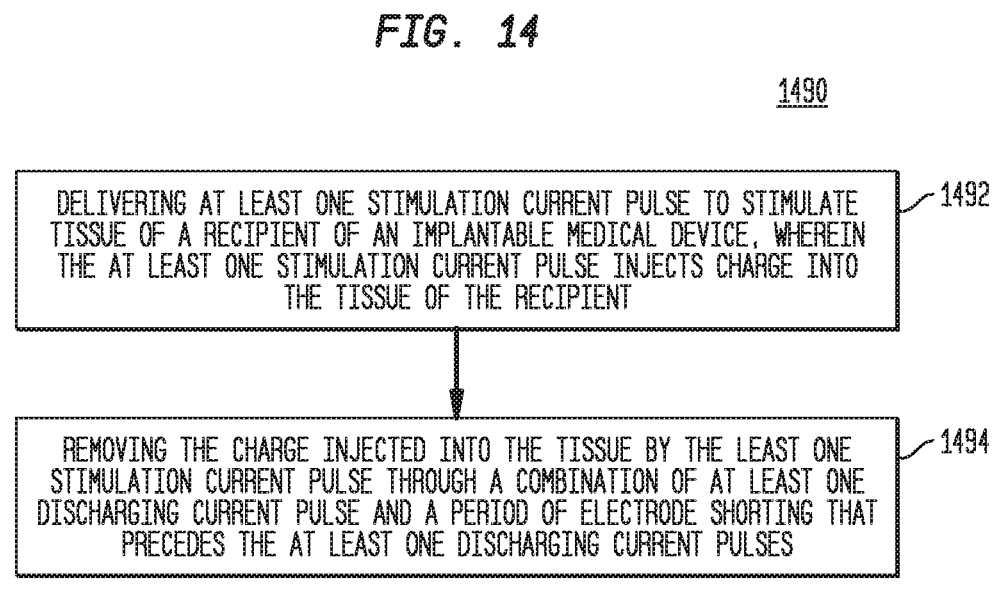

DELIVERING AT LEAST ONE STIMULATION CURRENT PULSE TO STIMULATE TISSUE OF A RECIPIENT OF AN IMPLANTABLE MEDICAL DEVICE, WHEREIN THE AT LEAST ONE STIMULATION CURRENT PULSE INJECTS CHARGE INTO THE TISSUE OF THE RECIPIENT — 1492

REMOVING THE CHARGE INJECTED INTO THE TISSUE BY THE LEAST ONE STIMULATION CURRENT PULSE THROUGH A COMBINATION OF AT LEAST ONE DISCHARGING CURRENT PULSE AND A PERIOD OF ELECTRODE SHORTING THAT PRECEDES THE AT LEAST ONE DISCHARGING CURRENT PULSES — 1494

HYBRID MULTI-PHASIC STIMULATION

BACKGROUND

Field of the Invention

The present invention relates generally to the electrical stimulation in implantable medical device.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, a method is provided. The method comprises: delivering, via at least one of a plurality of implantable electrodes of an implantable medical device, a stimulation current pulse to inject charge into tissue of a recipient of the implantable medical device; shorting the at least one of the plurality of implantable electrodes with one or more other of the plurality of implantable electrodes to remove a first portion of the charge injected into the tissue by the stimulation current pulse; and delivering at least one discharging current pulse to the tissue of the recipient to remove a second portion of the charge injected into the tissue by the stimulation current pulse.

In another aspect, an implantable medical device is provided. The implantable medical device comprises: a plurality of electrodes configured to be implanted adjacent to tissue of a recipient; and a stimulation subsystem configured to generate a plurality of hybrid multi-phasic stimulation signals for delivery via one or more of the plurality of electrodes, wherein each hybrid multi-phasic stimulation signal comprises at least one cathodic current pulse and at least one anodic current pulse, and wherein the at least one cathodic current pulse and at least one anodic current pulse are separated from one another by at least one shorting period.

In another aspect, a method is provided. The method comprises: delivering at least a first current pulse to tissue of a recipient of an implantable medical device via at least one of a plurality of implantable electrodes, wherein the first pulse has a first current polarity and is configured to stimulate the tissue; delivering at least a second current pulse having a second current polarity to the tissue of the recipient, wherein the second current polarity is an opposite current polarity to the first current polarity; and prior to delivering the at least one discharging current pulse, shorting the at least one of the plurality of implantable electrodes with one or more other of the plurality of implantable electrodes.

In another aspect, a method is provided. The method comprises: delivering at least one stimulation current pulse to stimulate tissue of a recipient of an implantable medical device, wherein the at least one stimulation current pulse injects charge into the tissue of the recipient; and removing the charge injected into the tissue by the least one stimulation current pulse through a combination of at least one discharging current pulse and a period of electrode shorting that precedes the at least one discharging current pulse.

BRIEF DESCRIPTION OF THE DRAWINGS

Embodiments of the present invention are described herein in conjunction with the accompanying drawings, in which:

FIG. 3 is a schematic diagram illustrating an example monophasic stimulation signal;

FIG. 6 is a schematic diagram illustrating another example hybrid multi-phasic stimulation signal, in accordance with certain embodiments presented herein;

FIG. 7 is a schematic diagram illustrating another example hybrid multi-phasic stimulation signal, in accordance with certain embodiments presented herein;

FIG. 11 is a schematic diagram illustrating a vestibular implant, in accordance with certain embodiments presented herein;

FIG. 12 is a flowchart of a method, in accordance with certain embodiments presented herein;

FIG. 14 is a flowchart of another method, in accordance with certain embodiments presented herein.

DETAILED DESCRIPTION

Presented herein are hybrid multi-phasic stimulation techniques for stimulation of tissue of a recipient of an implantable medical device. In particular, in accordance with the hybrid multi-phasic stimulation techniques, at least one stimulation current pulse is delivered to the tissue of the recipient in order to stimulate the tissue. The at least one stimulation current pulse injects charge into the tissue that is then removed through the combination of at least one discharging current pulse and a period of electrode shorting.

Merely for ease of description, the hybrid multi-phasic stimulation techniques presented herein are primarily described with reference to a specific implantable medical device system, namely a cochlear implant system. However, it is to be appreciated that the hybrid multi-phasic electrical stimulation techniques presented herein may also be implemented by other types of implantable medical devices or implantable medical device systems. For example, the hybrid multi-phasic electrical stimulation techniques may be implemented by other auditory prostheses or systems includes other auditory prostheses, such as middle ear auditory prostheses, bone conduction devices, direct acoustic stimulators, electro-acoustic prostheses, auditory brain stimulators, etc. The techniques presented herein may also be used with tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Figure 1A:
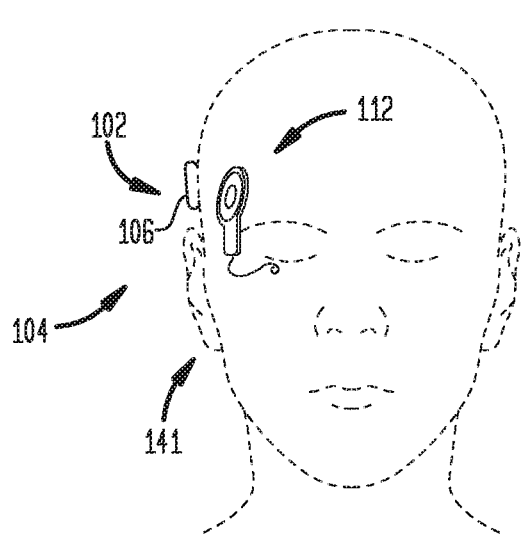
FIG. 1A is a schematic diagram illustrating a cochlear implant system, in accordance with certain embodiments presented herein.
Figure 1B:
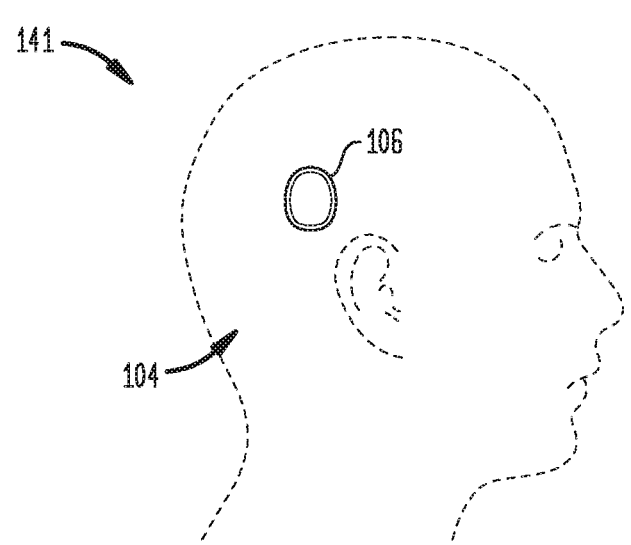
FIG. 1B is a side view of a recipient wearing a sound processing unit of the cochlear implant system of FIG. 1A.
Figure 1C:
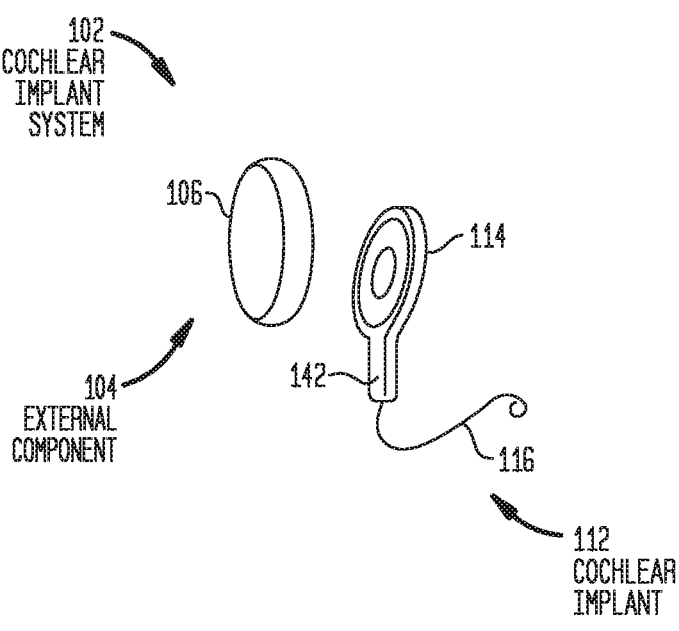
FIG. 1C is a schematic view of components of the cochlear implant system of FIG. 1A.
Figure 1D:
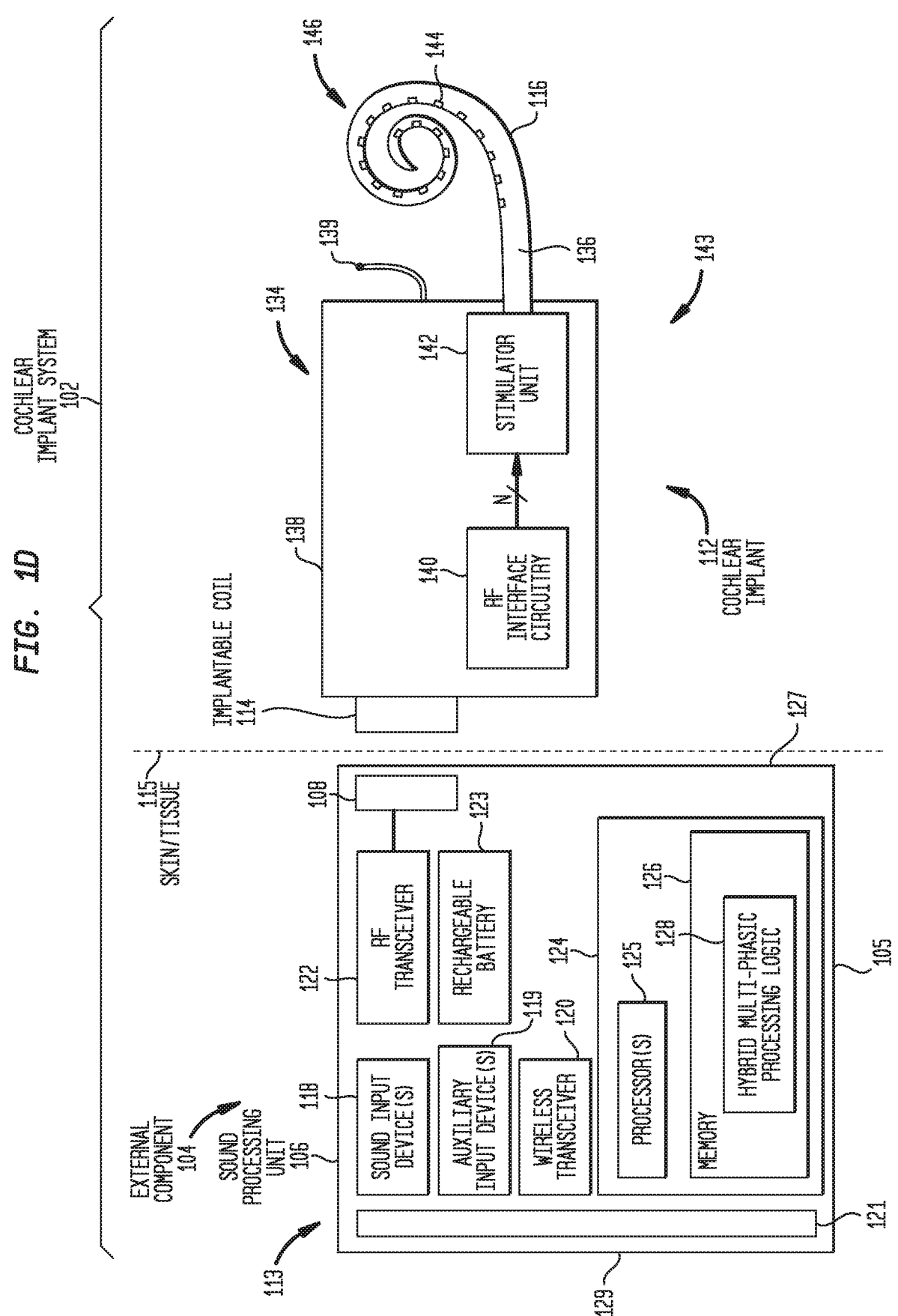
FIGS. 1D is a block diagram of the cochlear implant system of FIG. 1A.

FIGS. 1A-1D are diagrams illustrating an example cochlear implant system 102 configured to implement certain embodiments of the techniques presented herein. The cochlear implant system 102 comprises an external component 104 and an implantable component 112. In the examples of FIGS. 1A-1D, the implantable component is sometimes referred to as a "cochlear implant." FIG. 1A is a schematic diagram illustrating the implantable component 112 implanted in the head 141 of a recipient, while FIG. 1B is schematic drawing of the external component 104 worn on the head 141 of the recipient. FIG. 1C is another schematic view of the cochlear implant system 102, while FIG. 1D is a block diagram illustrating further details of the cochlear implant system 102. For ease of description, FIGS. 1A-1D will generally be described together.

As noted, cochlear implant system 102 includes an external component 104 that is configured to be directly or indirectly attached to the body of the recipient and an implantable component 112 configured to be implanted in the recipient. In the examples of FIGS. 1A-1D, the external component 104 comprises a sound processing unit 106, while the implantable component 112 includes an internal coil 114, a stimulator unit 142, and an elongate stimulating assembly 116 configured to be implanted in the recipient's cochlea.

In the example of FIGS. 1A-1D, the sound processing unit 106 is an off-the-ear (OTE) sound processing unit, sometimes referred to herein as an OTE component, that is configured to send data and power to the implantable component 112. In general, an OTE sound processing unit is a component having a generally cylindrically shaped housing 105 and which is configured to be magnetically coupled to the recipient's head (e.g., includes an integrated magnet configured to be magnetically coupled to a magnet in the implantable component 112). The OTE sound processing unit 106 also includes an integrated external coil 108 that is configured to be inductively coupled to the implantable coil 114.

It is to be appreciated that the OTE sound processing unit 106 is merely illustrative of the external devices that could operate with implantable component 112. For example, in alternative examples, the external component may comprise a behind-the-ear (BTE) sound processing unit or a micro-BTE sound processing unit and a separate external. In general, a BTE sound processing unit comprises a housing that is shaped to be worn on the outer ear of the recipient and is connected to the separate external coil via a cable assembly (cable), where the external coil is configured to be inductively coupled to the implantable coil 114. It is also to be appreciated that alternative external components could be located in the recipient's ear canal, worn on the body, etc.

FIGS. 1A-1D illustrate an arrangement in which the cochlear implant system 102 includes an external component. However, it is to be appreciated that embodiments of the present invention may be implemented in cochlear implant systems having alternative arrangements. For example, embodiments presented herein can be implemented by a totally implantable cochlear implant or other totally implantable medical device. A totally implantable medical device is a device in which all components of the device are configured to be implanted under skin/tissue of a recipient. Because all components are implantable, a totally implantable medical device operates, for at least a finite period of time, without the need of an external device. An external device can be used to, for example, charge the internal power source (battery).

Returning to the specific example of FIGS. 1A-1D, FIG. 1D illustrates that the OTE sound processing unit 106 comprises one or more input devices 113 that are configured to receive input signals (e.g., sound or data signals). The one or more input devices 113 include one or more sound input devices 118 (e.g., microphones, audio input ports, telecoils, etc.), one or more auxiliary input devices 119 (e.g., audio ports, such as a Direct Audio Input (DAI), data ports, such as a Universal Serial Bus (USB) port, cable port, etc.), and a wireless transmitter/receiver (transceiver) 120. However, it is to be appreciated that one or more input devices 113 may include additional types of input devices and/or less input devices (e.g., the wireless transceiver 120 and/or one or more auxiliary input devices 119 could be omitted).

The OTE sound processing unit 106 also comprises the external coil 108, a charging coil 121, a closely-coupled transmitter/receiver (transceiver) 122, sometimes referred to as or radio-frequency (RF) transceiver 122, at least one rechargeable battery 123, and a processing module 124. The processing module 124 comprises one or more processors 125 and a memory device (memory) 126 that includes hybrid multi-phasic processing logic 128. The memory device 126 may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The one or more processors 125 are, for example, microprocessors or microcontrollers that execute instructions for the hybrid multi-phasic processing logic 128 stored in memory device 126 (e.g., execute instructions for implementation of the hybrid multi-phasic stimulation techniques presented herein).

The implantable component 112 comprises an implant body (main module) 134, a lead region 136, and the intra-cochlear stimulating assembly 116, all configured to be implanted under the skin/tissue (tissue) 115 of the recipient. The implant body 134 generally comprises a hermetically-sealed housing 138 in which RF interface circuitry 140 and a stimulator unit 142 are disposed. The implant body 134 also includes the internal/implantable coil 114 that is generally external to the housing 138, but which is connected to the transceiver 140 via a hermetic feedthrough (not shown in FIG. 1D).

As noted, stimulating assembly 116 is configured to be at least partially implanted in the recipient's cochlea. Stimulating assembly 116 includes a plurality of longitudinally spaced intra-cochlear electrical stimulating contacts (electrodes) 144 that collectively form a contact or electrode array 146 for delivery of electrical stimulation (current) to the recipient's cochlea.

Stimulating assembly 116 extends through an opening in the recipient's cochlea (e.g., cochleostomy, the round window, etc.) and has a proximal end connected to stimulator unit 142 via lead region 136 and a hermetic feedthrough (not shown in FIG. 1D). Lead region 136 includes a plurality of conductors (wires) that electrically couple the electrodes 144 to the stimulator unit 142. The implantable component 112 also includes an electrode outside of the cochlea, sometimes referred to as the extra-cochlear electrode (ECE) 139.

As noted, the cochlear implant system 102 includes the external coil 108 and the implantable coil 114. Generally, a magnet is fixed relative to each of the external coil 108 and the implantable coil 114. The magnets fixed relative to the external coil 108 and the implantable coil 114 facilitate the operational alignment of the external coil 108 with the implantable coil 114. This operational alignment of the coils enables the external component 104 to transmit data and power to the implantable component 112 via a closely-coupled wireless link formed between the external coil 108 and the implantable coil 114. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1D illustrates only one example arrangement.

As noted above, sound processing unit 106 includes the processing module 124. The processing module 124 is configured to convert received input signals (received at one or more of the input devices 113) into output signals for use in stimulating a first ear of a recipient (i.e., the processing module 124 is configured to perform sound processing on input signals received at the sound processing unit 106). Stated differently, the one or more processors 125 are configured to execute hybrid multi-phasic processing logic 128 in memory 126 to convert the received input signals into output signals 145 that represent electrical stimulation for delivery to the recipient.

As described further below, electrical stimulation signals in accordance with embodiments presented can comprise hybrid multi-phasic stimulation signals. As such, the output signals 145 generated by the sound processing unit 106 represent the hybrid multi-phasic stimulation signals (e.g., comprise commands/data for use by the stimulator unit 142 to form hybrid multi-phasic stimulation signals).

As noted, FIG. 1D illustrates an embodiment in which the processing module 124 in the sound processing unit 106 generates the output signals. In an alternative embodiment, the sound processing unit 106 can send less processed information (e.g., audio data) to the implantable component 112 and the sound processing operations (e.g., conversion of sounds to output signals 145) can be performed by a processor within the implantable component 112. That is, the implantable component 112, rather than the sound processing unit 106, could include a processing module that is similar to processing module 124 of FIG. 1D.

Returning to the specific example of FIG. 1D, the output signals 145 are provided to the RF transceiver 122, which transcutaneously transfers the output signals (e.g., in an encoded manner) to the implantable component 112 via external coil 108 and implantable coil 114. That is, the output signals are received at the RF interface circuitry 140 via implantable coil 114 and provided to the stimulator unit 142. The stimulator unit 142 is configured to utilize the output signals to generate electrical stimulation signals (e.g., current signals) for delivery to the recipient's cochlea via "stimulation channels," where each stimulating channel comprises one or more of the stimulating contacts 144. In this way, cochlear implant system 102 electrically stimulates the recipient's auditory nerve cells, bypassing absent or defective hair cells that normally transduce acoustic vibrations into neural activity, in a manner that causes the recipient to perceive one or more components of the received sound signals.

As noted, the processing module 124 generates the output signals 145 which, in turn, are used by the stimulator unit 142 to generate current pulses and/or electrode shorting periods that, as described below, form hybrid multi-phasic stimulation signals presented herein. As such, the processing module 124 and the stimulator unit 142 are sometimes collectively referred to herein as a "stimulation subsystem" 143 that, in general, is configured to generate a plurality of hybrid multi-phasic stimulation signals for delivery via one or more of the plurality of electrodes 144.

In general, with electrical stimulation, the flow of anions (−) and cations (+) is controlled by the mechanics of the circuitry within the stimulator unit. In a stimulator unit, the cathode is considered the negative pole (−) because it discharges anions (−), while the anode is the positive pole (+) because it discharges cations (+). Therefore, depending on the configuration of the polarity of a stimulator at a given time, the stimulator will discharge either cations or anions into the body part being stimulated. In cathodic stimulation, anions (−) are discharged into the body as current flows from the cathode (−), through the tissue, and back to the anode (+). In anodal stimulation, cations (+) are discharged into the body as current flows from the anode (+), through the tissue, and back to the cathode (−).

In addition, electrical stimulation of the tissue (e.g., nerve cells) requires "charge balancing." That is, any charge delivered to the recipient's tissue must also be removed/withdrawn from the tissue, at least to a level such that there is a net average DC current flow below a predetermined threshold (e.g., approximately less than 100 nA).

Figure 2:
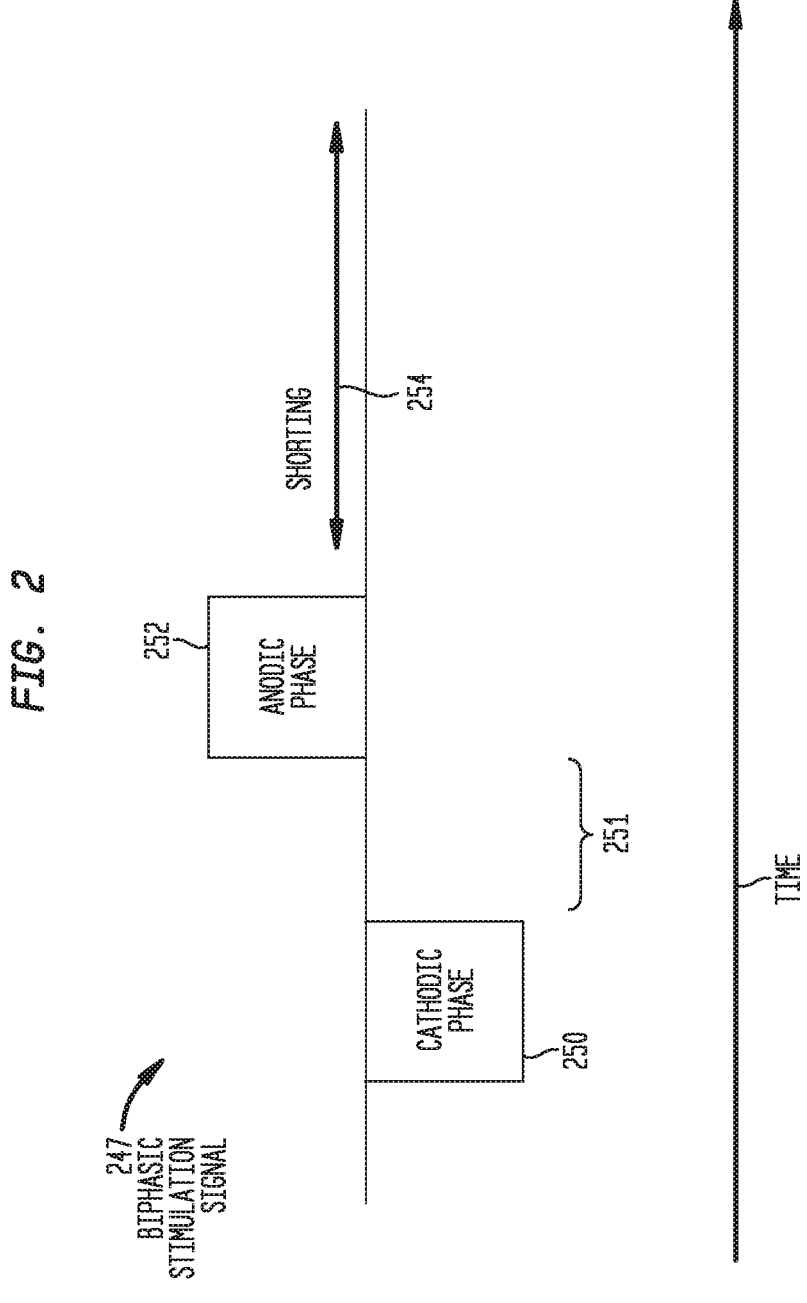
FIG. 2 is a schematic diagram illustrating an example biphasic stimulation signal.

As shown in FIG. 2, certain implantable medical devices use a biphasic stimulation signals 247 (biphasic stimulation) to ensure charge balancing. In conventional biphasic stimulation, the device's stimulation circuit (stimulator) delivers a first cathodic (−) current pulse 250 followed by a second anodic (+) current pulse 252 (or vice versa in alternative embodiments), where the first and second current pulses are generally "balanced." That is, the first and second current pulses are generally configured to inject substantially the same amount of charge, but with opposing polarities, into the tissue.

More specifically, the implantable medical device generates and injects the cathodic current pulse 250 into the electrode-tissue interface. The cathodic pulse 250 depolarizes axons in the recipient's tissue and, accordingly, triggers an action potential (e.g., with an auditory prosthesis such as cochlear implant system 102, the cathodic current pulse is the stimulating part that evokes a hearing perception).

As shown, the cathodic current pulse 250 is followed by an Inter Phase Gap (IPG) 251 (e.g., a time period in which no stimulation signals are delivered). After the IPG 251, the implantable medical device then generates and injects the anodic current pulse 252. The anodic pulse 252 injects a charge into the electrode-tissue interface to reverse the potentially damaging electrochemical processes that can occur at the electrode-tissue interface during delivery of the cathodic current pulse 250. That is, the cathodic pulse and the anodic current pulse are generally "balanced" in that they each inject similar charges (e.g., within about 5 percent of one another), but with opposite polarities, into the electrode-tissue interface. The end result is that the tissue is generally charge balanced.

As noted, the anodic current pulse 252 may be followed by a period 254 of shorting (shorting period) in which all the implantable electrodes are shorted together. In general, biphasic stimulation pulses (i.e., two sequential current pulses of opposite polarity, such as pulses 250 and 252) produce stimulation with close to zero net charge at the electrode-tissue interface (e.g., generally remove charge imbalance to a point to ensure a net average DC current flow below a predetermined threshold). As a result, the shorting period 254 is relatively short and may function as a safety mechanism. In conventional biphasic stimulation, the shorting period 254 has a predetermined length (no feedback loop).

Since the anodic current pulse 252 is configured to balance the charge injected by the cathodic current pulse 250, the anodic current pulse 252 is generated with a current source and generally requires a similar amount of energy from the implant power supply as the cathodic current pulse. That is, nearly half of the power consumed through biphasic stimulation is consumed through generation of the second polarity current pulse (e.g., the anodic current pulse 252) which merely removes charge from the tissue. Since, in biphasic stimulation the shorting period 254 is relatively short, biphasic stimulation is well suited for use with higher stimulation rate stimulation strategies/paradigms.

Figure 3:
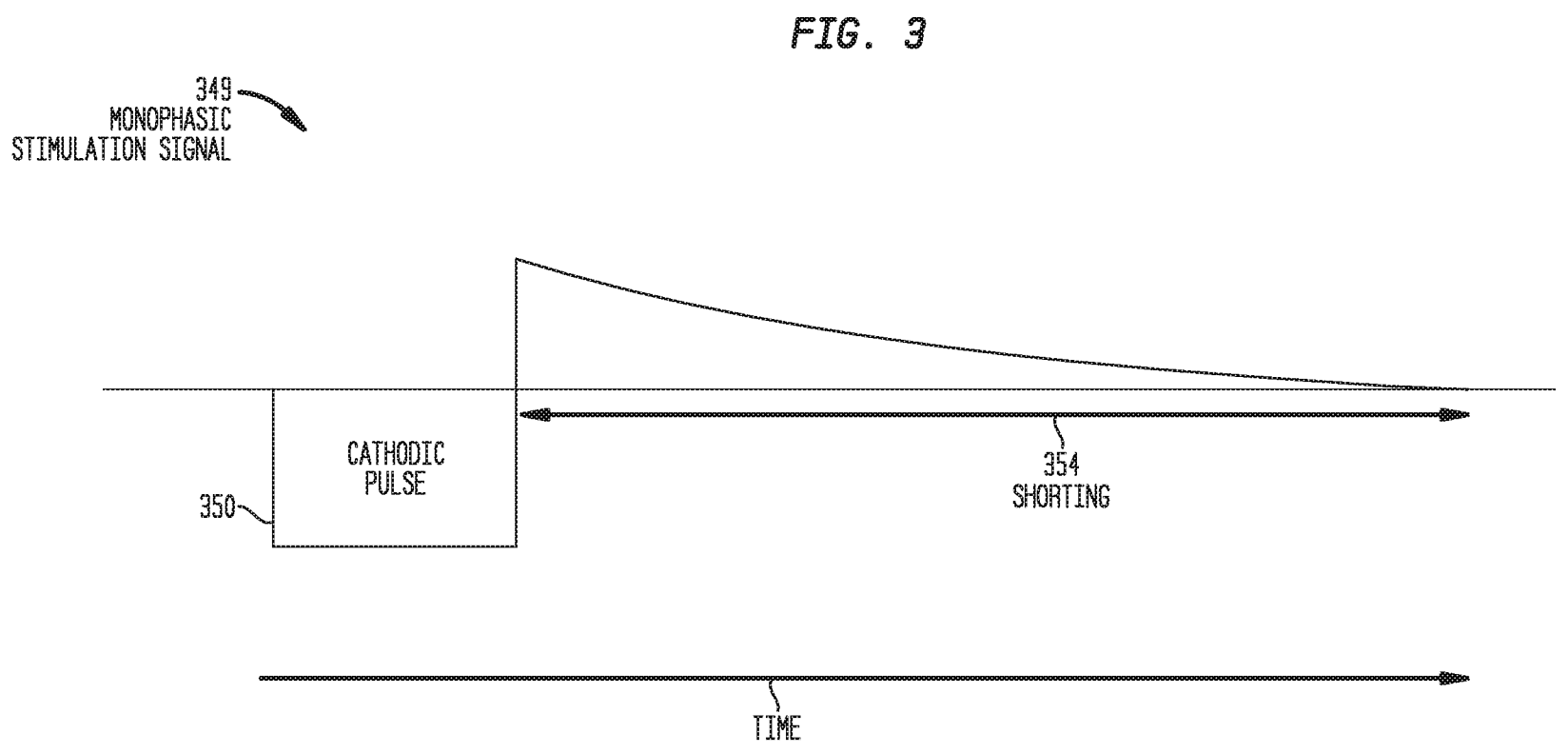

Almost half of the stimulation power used on biphasic stimulation can be saved by the use of monophasic stimulation in which the anodic pulse is replaced by a long electrode shorting period. That is, shown in FIG. 3 is a monophasic stimulation signals 349 where the implantable medical device (e.g., cochlear implant system 102) only generates a cathodic current pulse 350 (or only an anodic pulse in alternative embodiments) and replaces the anodic current pulse with a longer period 354 of shorting (shorting period) that immediately follows the cathodic current pulse 350. In conventional monophasic stimulation, the shorting period 354 has a predetermined length (no feedback loop).

The advantage of monophasic stimulation is that the shorting period 354 requires no stimulation energy from the implantable medical device and, as such, stimulation power is almost halved relative to biphasic stimulation. As is the case with biphasic stimulation, the length of the shorting period 354 needs to be sufficiently long (e.g., have a time length) so as to extract the injected charge and keep the average net DC current to below a predetermined threshold, such as approximately less than 100 nA. Stated differently, the shorting period 354 has a time length that is sufficient to ensure removal of remaining charge imbalance, at least to a point to ensure a net average DC current flow below a predetermined threshold. A disadvantage of monophasic stimulation is that the time length of the shorting period 354 can be very long in order for the charge to decay to an acceptable level which, in turn limits the use of monophasic stimulation with higher stimulation rate stimulation strategies.

As described above, biphasic stimulation and monophasic stimulation each have associated advantages and disadvantages. In particular, whereas the brief shorting period makes biphasic stimulation well suited can be used with higher stimulation rate stimulation strategies/paradigms, biphasic stimulation also consumes a significant amount of power simply for the purposes of charging balancing. In addition, monophasic stimulation does not consume power for the purposes of charging balancing, the long shorting period monophasic stimulation limits the use of the monophasic stimulation with higher stimulation rate stimulation strategies.

Presented herein are hybrid multi-phasic stimulation techniques that provide the reduced power benefits of monophasic stimulation with a shorter stimulation signal time duration that enables the use of higher stimulation rate stimulation strategies (e.g., a time duration that is shorter than monophasic stimulation). More specifically, referring specifically to the arrangement of FIGS. 1A-1D, the cochlear implant system 102 is configured to generate one or more "hybrid multi-phasic stimulation signals" based on one or more received sound signals. As used herein, each "hybrid multi-phasic stimulation signal" comprises at least a first current pulse having a first current polarity followed by at least a second current pulse having a second (opposing) current polarity and a shorting period. In addition, the first and second current pulses in the hybrid multi-phasic stimulation signal are "unbalanced" or "non-charge balancing," meaning that the charge injected by the second current pulse is intentionally less than the charge injected by the first current pulse. As such, the energy/power required to generate the second current pulse is lower than the energy required to generate the first current pulse. As described further below, in certain embodiments a hybrid multi-phasic stimulation signal may also include one or more additional shorting periods and/or one or more additional current pulses.

As described further below, the hybrid multi-phasic stimulation techniques presented herein may be particularly advantageous with multipolar stimulation strategies where multiple stimulation signals are simultaneously delivered via multiple different electrodes (e.g., multiple electrodes stimulating at the same time). The power requirements associated with known and future multipolar stimulation strategies appear to be many times greater than monopolar stimulation.

Figure 4A:
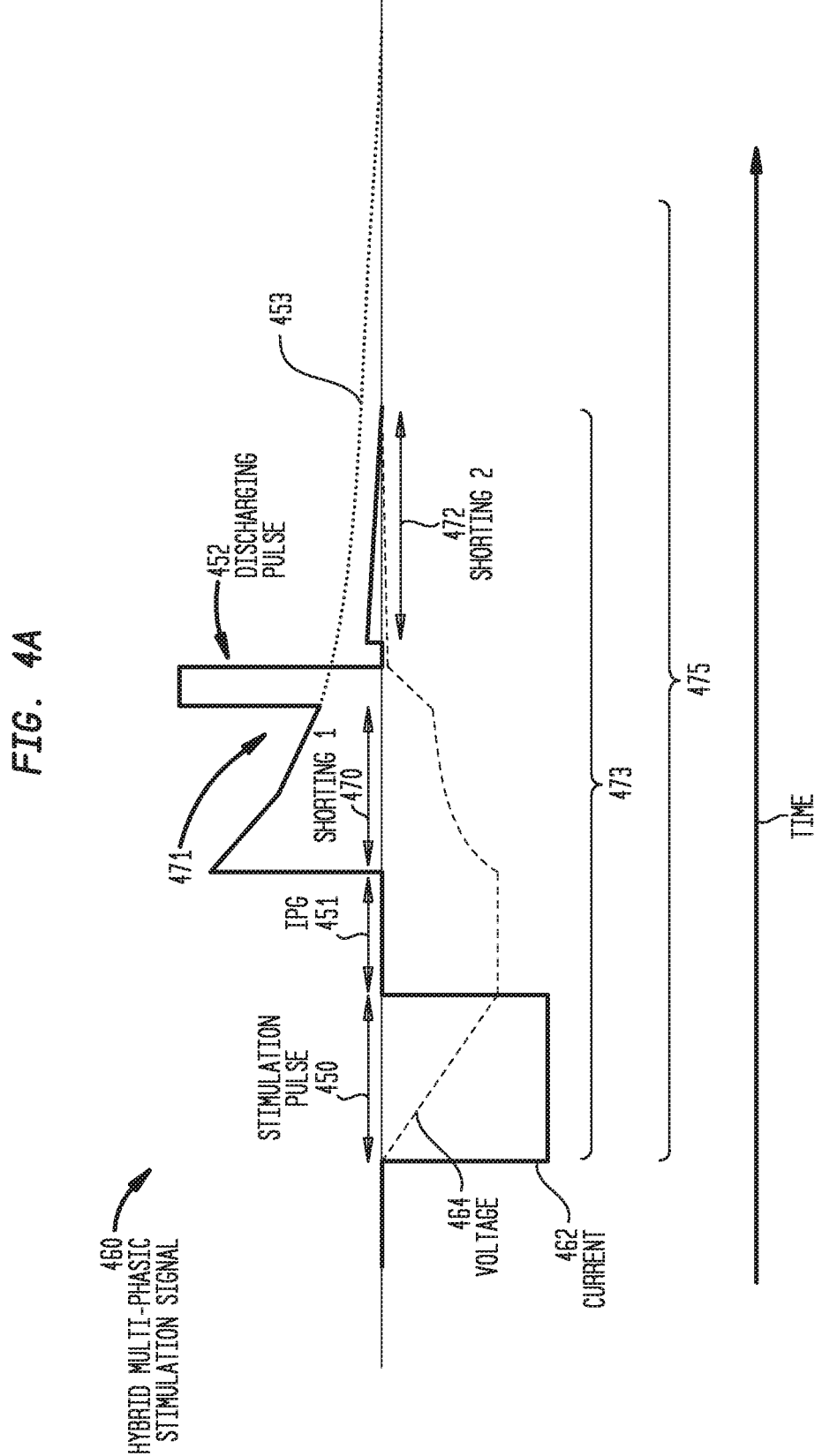
FIGS. 4A and 4B are schematic diagrams illustrating an example hybrid multi-phasic stimulation signal, in accordance with certain embodiments presented herein.
Figure 4B:
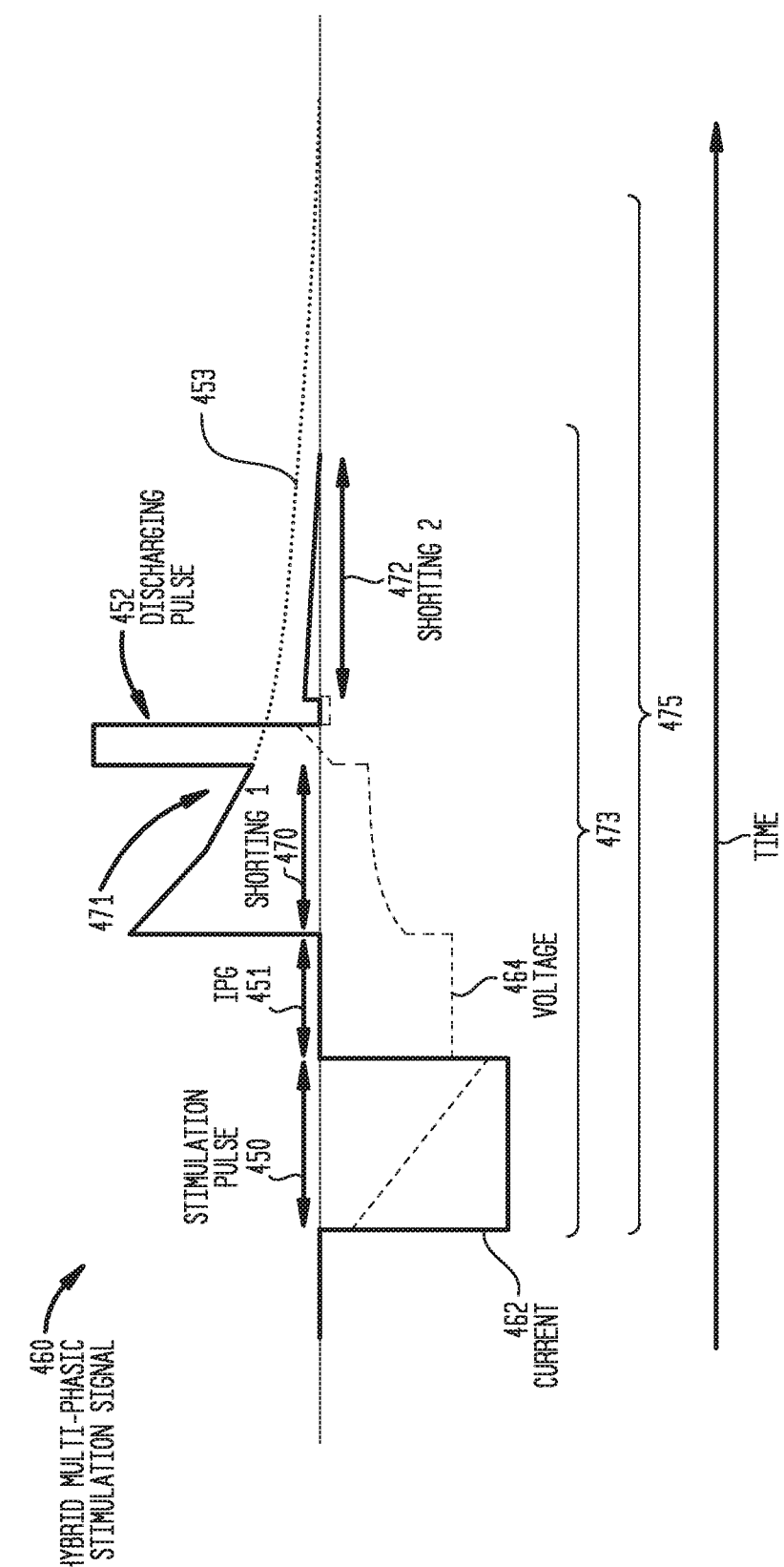

FIGS. 4A and 4B are schematic diagrams illustrating an example hybrid multi-phasic stimulation signal 460 in accordance with embodiments presented herein. For ease of description, the examples of FIGS. 4A and 4B will generally be described with reference to the cochlear implant system 102 of FIGS. 1A-1D. However, as explained elsewhere herein, the hybrid multi-phasic stimulation techniques may be applied in a variety of contexts and may be implemented by a number of different implantable medical devices and/or different implantable medical device systems.

FIGS. 4A and 4B each include a first curve/trace 462 illustrating the current associated with the hybrid multi-phasic stimulation signal 460 at the interface between the implanted electrodes 144 and the recipient's cochlea (e.g., the electrode-tissue interface). Stated differently, curve 462 illustrates the instantaneous current injected or withdrawn from the electrode-tissue interface, over time. FIGS. 4A and 4B each also include a second curve/trace 464 illustrating the voltage associated with the with the hybrid multi-phasic stimulation signal 460 at the electrode-tissue interface. That is, curve 464 illustrates the instantaneous voltage at the electrode-tissue interface, over time.

In FIG. 4A, the voltage curve 464 is shown in a simplified form that ignores current times resistance (IR) offset. FIG. 4B illustrates the voltage curve 464 so as to include the IR offset. For ease of illustration and understanding, the embodiments of FIGS. 4A-4B will generally be described with reference to the simplified illustration of FIG. 4A. In addition, the other embodiments presented herein will also be illustrated in the simplified form that ignores IR offset on the voltages.

Returning to the specific example of FIGS. 4A and 4B, the hybrid multi-phasic stimulation signal 460 begins with a first current pulse 450 having a first polarity. In this example, the first current pulse 450 is a cathodic (−) current pulse (e.g., stimulator unit 142 is configured to discharge anions (−) into the electrode-tissue interface). The first current pulse 450 is the portion of the hybrid multi-phasic stimulation signal 460 that evokes a percept from the recipient (i.e., the portion of the signal that depolarizes axons and triggers an action potential). As such, in this example, the first current pulse 450 is sometimes referred to herein as a "stimulation pulse" and the hybrid multi-phasic stimulation signal 460 is sometimes referred to herein as a "cathodic hybrid multi-phasic stimulation signal."

As shown in FIGS. 4A and 4B, the first current pulse 450 is followed by an Inter Phase Gap (IPG) 451, which is a time period in which no current is delivered to, or withdrawn from, the electrode-tissue interface. The IPG 451 may have a predetermined, dynamically determined or variable duration as the longer the duration of the IPG, the lower the critical/firing threshold (at least for biphasic pulses) of the stimulated nerve cells. In general, the critical threshold of a nerve cell is the current level that causes the nerve cell to become depolarized beyond the cell's critical threshold, thereby causing the nerve cell to undergo an action potential. This action potential is sometimes referred to as the "firing" of the nerve cell.

In accordance with the hybrid multi-phasic stimulation techniques presented herein, the IPG 451 is followed by a first period 470 of shorting (shorting period) during which all the implantable electrodes 144 are "shorted" together. As used herein, reference to "shorting" of implantable electrodes, such as electrodes 144, means that all of the electrodes are connected together to a same low impedance (e.g., connected together internally within the implantable medical device). Since the electrodes are all connected to the same low impedance, the shorting, if enabled for a sufficient period of time, dissipates any charge at the electrode-tissue interface. That is, the shorting of the electrodes withdraws residual charge from the electrode-tissue interface (e.g., brings all of the electrodes to the same potential, if a shorting period is sufficiently long).

As noted above, monophasic stimulation relies upon a long shorting period to withdraw residual charge from the electrode-tissue interface. However, also as noted above, although a long shorting period is energy efficient (e.g., does not require any power to remove the charge), a long shorting period is also not useable with higher rate stimulation strategies. As such, the shorting period 470 has a short time length that is sufficient to withdraw only part of the residual charge from the tissue-electrode interface. That is, as shown in FIGS. 4A and 4B, at the end 471 of the shorting period 470, a residual charge remains at the electrode-tissue interface.

To remove or substantially reduce the residual charge remaining at the electrode-tissue interface, the hybrid multi-phasic stimulation signal 460 comprises a second current pulse 452 (current pulse) having a second polarity (e.g., an opposing polarity to the first polarity of the first current pulse 450). As noted, in the example of FIGS. 4A and 4B, the first current pulse 450 is a cathodic pulse. As such, in this example, the second current pulse 452 is an anodic pulse (e.g., the stimulator unit 142 is configured to discharge cations (+) into the electrode-tissue interface). Since, in this example, the second current pulse 452 is the portion of the hybrid multi-phasic stimulation signal 460 that balances residual charge, the anodic current pulse 452 is sometimes referred to herein as a "discharging pulse."

As noted above, the shorting period 470 is provided between the first current pulse 450 and second current pulse 452 and removes some of the charge introduced into the electrode-tissue interface by the first current pulse 450. That is, at the beginning of the second current pulse 452, some charge has already been removed from the electrode-tissue interface. As a result, since the second current pulse 452 does not have to discharge all of the charge introduced by the cathodic pulse 450, the second current pulse 452 has a time length (and/or amplitude) that is less than the first current pulse 450. That is, the first current pulse 450 and the second current pulse 452 are "unbalanced," meaning that the charge discharged by the second current pulse 452 is not the same as the charge introduced by the first current pulse 450. Instead, the charge removed by the combination of the shorting period 470 and the second current pulse 452 is generally equivalent to the charge introduced by the cathodic pulse 450. Stated differently, the shorting period 470 and the anodic pulse 452 are collectively configured to "balance" the charge at the electrode-tissue interface.

In general, the techniques presented herein allow for control of the percentage of charge removed by the shorting period by varying the length of the shorting period. There is a tradeoff between overall shorting length (and stimulation duration/rate) and power saved where a brief shorting duration reduces overall stimulation duration, but also reduces power savings. In accordance with certain embodiments presented herein, the shorting period 470 removes approximately at least 10 percent (%) of the charge introduced by the first current pulse 450. In accordance with other embodiments presented herein, the shorting period 470 removes approximately at least 25 percent (%) of the charge introduced by the first current pulse 450. In other embodiments, the shorting period 470 removes approximately at least 50 percent (%) of the charge introduced by the first current pulse 450. In further embodiments, the shorting period 470 removes approximately at least 70 percent (%) of the charge introduced by the first current pulse 450. In still further embodiments, the shorting period 470 removes approximately at least 80 percent (%) of the charge introduced by the first current pulse 450. In still further embodiments, the shorting period 470 removes approximately at least 90 percent (%) of the charge introduced by the first current pulse 450. Since the charge discharged by the second current pulse 452 is not the same as the charge introduced by the first current pulse 450, the second current pulse 452 is sometimes referred to as an "abbreviated" or "condensed" discharging pulse. Similarly, since the charge withdrawn by the shorting period 470 is not the same as the charge introduced by the cathodic pulse 450, the shorting period 470 is sometimes referred to as an "abbreviated" or "condensed" shorting period.

In the example of FIGS. 4A and 4B, the hybrid multi-phasic stimulation signal 460 also includes a second period of shorting 472 (second shorting period) after the second current pulse 452. The second shorting period 472 may operate as a safety mechanism to, in certain examples, ensure that the residual charge at the electrode-tissue interface is reduced at least to a level such that there is a net average DC current flow below a predetermined threshold.

The presence of the second shorting period 472 increases the time length of the hybrid multi-phasic stimulation signal 460. As such, it may be advantageous to adaptively eliminate the second shorting period 472. To this end, in certain examples, the cochlear implant system 102 is configured to measure the voltage 464 at the electrode-tissue interface after the second current pulse 452. By performing a plurality of such measurements over time (e.g., during a plurality of different hybrid multi-phasic stimulation signals), the cochlear implant system 102 can adapt future stimulation signals (e.g., adapt the attributes of future discharging pulses) in a manner that ensures future shorting period 470 and the second current pulses 452 can ensure the residual charge at the electrode-tissue interface is reduced at least to a level such that there is a net average DC current flow below a predetermined threshold, without the need for the second shorting period.

Stated differently, any error in the size of the discharging pulse must be accommodated by a subsequent shorting period that adds time to the stimulation and potentially limits the stimulation rate. In certain examples, the stimulation subsystem 143 includes a feedback mechanism (feedback system) that can capture voltage measurements during certain hybrid multi-phasic signals (e.g., following delivery of stimulation current pulses) and use the voltage measurements to adaptively adjust the size of subsequent discharging pulses (amplitude and or duration) to ensure the average charge delivery is zero (e.g., feedback system that can alter the charge distribution in a following stimulation to, on average, account for imbalances) This will reduce the need for, and potentially eliminate, the final shorting period.

FIGS. 4A and 4B include a curve 453 illustrating removal of the charge in accordance with standard monophasic stimulation (e.g., without the abbreviated discharging pulse 452 and in accordance with monophasic stimulation signal 349 of FIG. 3). As can be seen from curve 453, the hybrid multi-phasic stimulation signal 460 has a total time length 473 that is shorter than a time length 475 of a standard monophasic stimulation signal (e.g., monophasic stimulation signal 349).

FIGS. 4A and 4B have been primarily described with reference to a time length difference between the first current pulse 450 and the second current pulse 452 that makes the two current pulses unbalanced. However, it is to be appreciated that the charge imbalance between the first current pulse 450 and the second current pulse 452 may be a result of other signal attributes, such as different amplitudes, a combination of different amplitudes and different time lengths, etc. In addition, the tissue slowly dissipates charge by itself, which leads to a very small imbalance, the effect of which is very small in short time frames.

In the example of FIGS. 4A and 4B, cochlear implant system 102 generates the first current pulse 450 to trigger action potentials in the recipient's auditory neurons (e.g., based on received sound signals). After the IPG 451, the cochlear implant system 102 initiates the initial shorting period 470 to remove an amount of the charge at the electrode-tissue interface. Once the voltage 464 drops to a predetermined level (e.g., approximately 10% of its peak value, approximately 25% of its peak value, approximately 50% its peak value, approximately 75% of its peak value, approximately 90%, of its peak value, etc.), the cochlear implant system 102 generates the abbreviated (low energy) second pulse 452 to accelerate the removal of the remaining stored charge.

Although the abbreviated anodic pulse 452 does require consume some power from the cochlear implant system 102, the power consumed is significantly less than a full anodic pulse used in a typical biphasic stimulation strategy. When the electrode-tissue interface is approximated as a capacitor, then the energy stored at the electrode-interface (E) is given as shown below in Equation 1.

$$E = \tfrac{1}{2} CV^2, \qquad\qquad \text{Equation 1:}$$

where C is the charge at the electrode-tissue interface and V is the voltage at the electrode-tissue interface.

As noted, this energy is injected during the first current pulse 450 and has to be extracted by the combination of the shorting period 470 and the second current pulse 452. For example, if the initial shorting period 470 were to reduce the voltage across the electrode-tissue interface (acting as a capacitor) to a half of the peak value, then the energy required to fully discharge the electrode-tissue interface is only one quarter of the energy required by the anodic pulse in typical biphasic stimulation.

As noted, at the end of the hybrid multi-phasic stimulation signal 460, the remaining/residual charge must be at least at level such that there is a net average DC current flow below a predetermined threshold (e.g., approximately less than 100 nA). As such, the charge to be injected with the second current pulse 452 must be coordinated with the charge withdrawn via the shorting period 470 as any error (positive or negative) in the anodic charge injection will need to be dissipated in the second shorting period 472. Therefore, a larger error in the second current pulse 452 requires a longer second shorting period 472, which in turn makes the hybrid multi-phasic stimulation signal 460 less suited for higher stimulation rate strategies. Similarly, the second shorting period 472 can be totally avoided if the anodic charge injection of the discharging pulse 452 is accurate enough to ensure an average DC current below the predetermined threshold (e.g., less than 100 nA).

For a rectangular current pulse, the injected charge is equal to the current amplitude times the duration. Stated more generally, the injected charge is equal to the time integral of the current. The current amplitude and the pulse duration can be adjusted (one up, the other down), while still ensuring that the correct total charge is delivered. Given the above, several different techniques can be applied to determine the charge to be injected via the abbreviated discharging pulse.

In certain examples, the charge to be injected via the abbreviated discharging pulse can be a pre-calculated/predetermined amount of charge determined based on measured impedance. For example, during fitting of the cochlear implant system 102, the impedances of the electrodes (electrode impedances) are calculated. The charge that the abbreviated discharging pulse needs to provide to bring the total stimulation charge to zero can be calculated (estimated) based on the electrode impedance and pre-determined values that are the result of, for example, testing during design of the system. A lookup table or equation with inputs of impedance, stimulation amplitude, stimulation pulse duration, and shorting duration can be used to determine the required charge for the abbreviated discharging pulse, where the needed charge is given as shown below in Equation 2.

$$\text{Charge=f(impedance, stimulation amplitude, stimulation pulse duration, shorting duration).} \qquad \text{Equation 2:}$$

In certain examples, the charge to be injected via the abbreviated discharging pulse can be dynamically determined based on the instantaneous voltage of the stimulating electrode, after the first stimulation pulse of the stimulation signal. That is, in the example of FIGS. 4A and 4B, the cochlear implant system 102 is configured to dynamically measure the electrode voltage 464 after the cathodic pulse 450. In addition, after the shorting period 470 (i.e., at 471), the cochlear implant system 102 is configured to measure the electrode voltage 464 and these voltages are used to calculate the required charge to be removed via the abbreviated discharging pulse 452 (e.g., calculate the charge needed to bring the total stimulation charge to zero), where the needed charge is given as shown below in Equation 3.

$$\text{Charge=f(electrode voltage).} \qquad \text{Equation 3:}$$

As noted above an implantable medical device in accordance with embodiments presented herein is configured to sequentially deliver a plurality of hybrid multi-phasic stimulation signals to a recipient. In certain embodiments, the implantable medical device is configured to measure the voltages during each hybrid multi-phasic stimulation signal (e.g., after each cathodic pulse and shorting period). However, in other embodiments, to simplify the design or save power, the voltage could be measured in every $n^{th}$ hybrid multi-phasic stimulation signal (e.g. only measure the voltage in a subset of the plurality of hybrid multi-phasic stimulation signals). For hybrid multi-phasic stimulation signals during which the voltage is not measured, the charge to be removed via the abbreviated discharging pulse could be estimated based on the stimulation pulse charge (known) and knowledge of the required discharging pulse charge for similar previous stimulation pulses.

Each of the above methods have associated errors. However, these errors could be reduced over time through the use of dynamic feedback techniques. For example, the errors could be reduced over time by measuring the electrode voltage after the abbreviated discharging pulse(s) and using these voltages to adjust the charge delivered by the brief discharge pulse by a small delta. Therefore, over time, the measured electrode voltage tends towards zero and the residual charge tends towards zero.

In the example of FIGS. 4A and 4B, the shorting period 470 occurs between the first current pulse 450 and the second current pulse 452. As such, in this example, the shorting period 470 is sometimes referred to as an "intra-pulse" shorting period. In other embodiments, the second current pulse 452 could precede the shorting period 470. Such an example is shown in FIG. 4C.

Figure 4C:
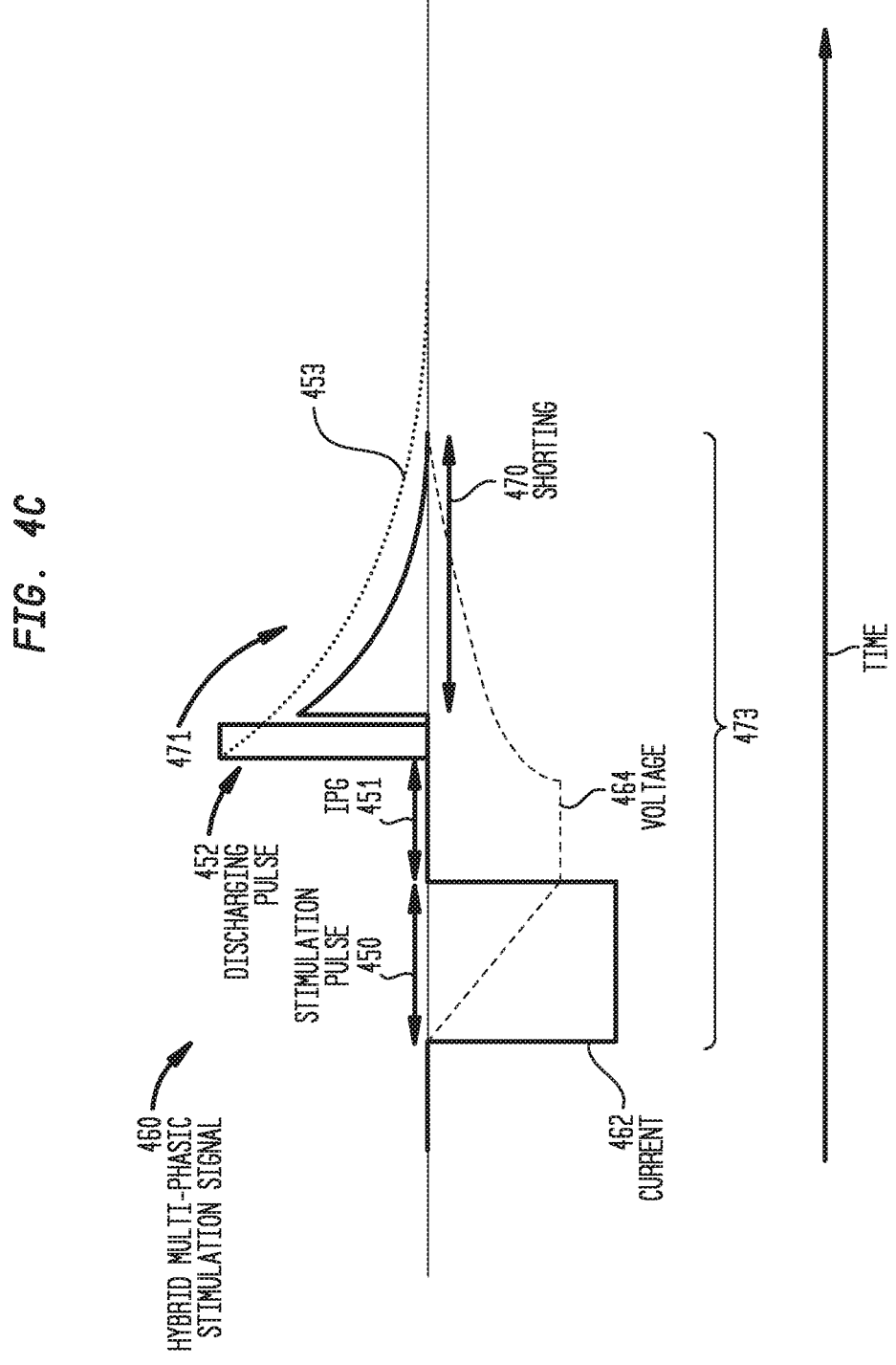
FIG. 4C is a schematic diagram illustrating another example hybrid multi-phasic stimulation signal, in accordance with certain embodiments presented herein.

More specifically, FIG. 4C is a schematic diagram illustrating an example hybrid multi-phasic stimulation signal 460(C) in accordance with embodiments presented herein. Hybrid multi-phasic stimulation signal 460(C) is similar to hybrid multi-phasic stimulation signal 460 except that the abbreviated discharging pulse 452 precedes the shorting period 470. In this example, the shorting periods 472 is omitted (e.g., combined with the shorting period 470).

FIGS. 4A, 4B, and 4C have generally been described above with reference to rectangular shaped current pulses. Is to be appreciated that the use of rectangular shaped current pulses in the embodiments of FIGS. 4A, 4B, and 4C, as well as in other embodiments, is merely illustrate and that the techniques presented herein may be implemented with current pulses having other shapes (e.g., triangular current pulses, ramped current pulses, etc.).

As noted, FIGS. 4A, 4B, and 4C generally illustrate "cathodic" hybrid multi-phasic stimulation signals 460 and 460(C) where the stimulation pulse 450 is a cathodic pulse and the abbreviated discharging pulse 452 is an anodic pulse. It is to be appreciated that the techniques presented herein may also be implemented with so-called "anodic" stimulation where the stimulation pulse is an anodic pulse and the abbreviated discharging pulse is a cathodic pulse.

Figure 5:
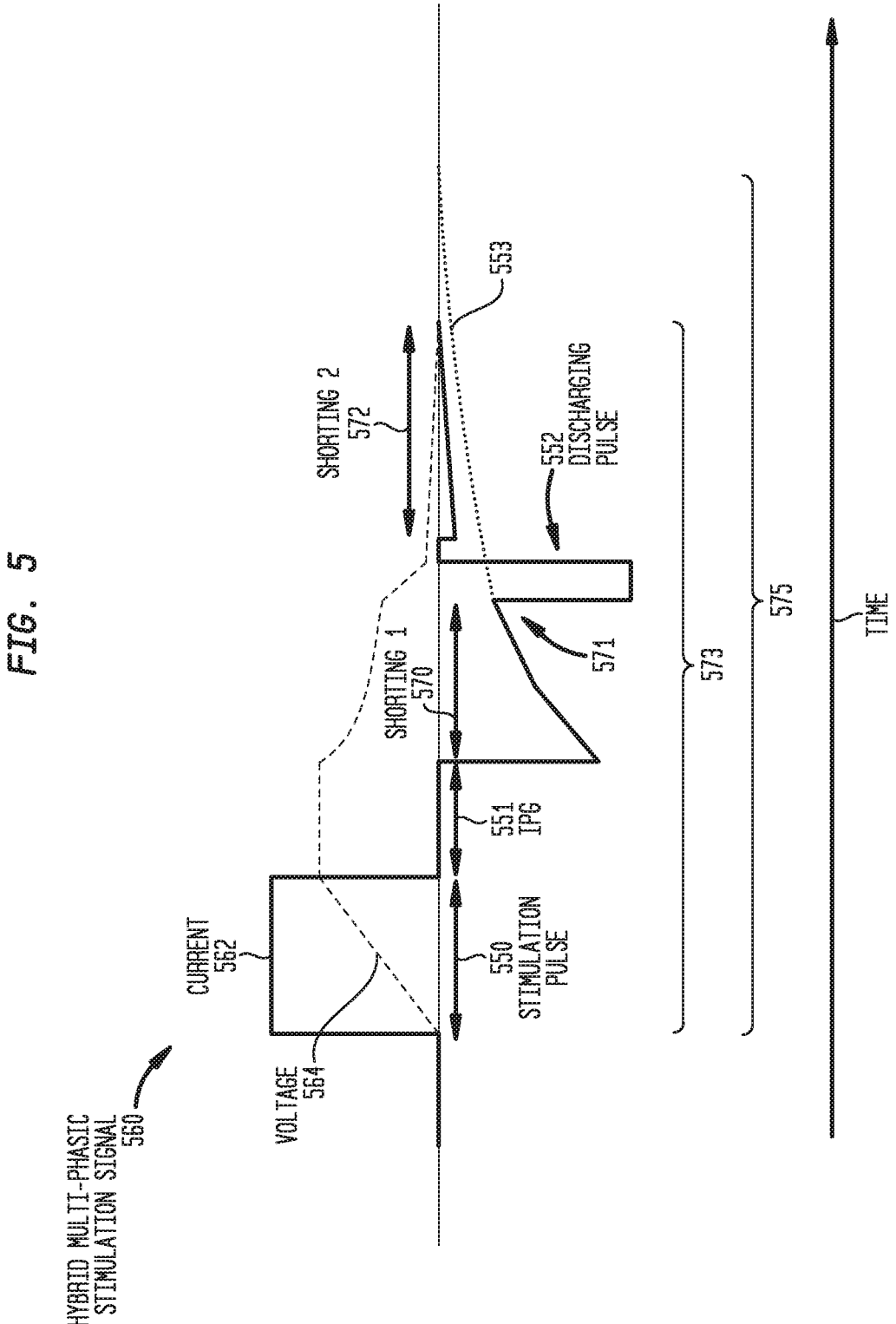
FIG. 5 is a schematic diagram illustrating another example hybrid multi-phasic stimulation signal, in accordance with certain embodiments presented herein.

For example, FIG. 5 is a schematic diagram illustrating an example hybrid multi-phasic stimulation signal 560 in accordance with such embodiments presented herein. For ease of description, the example of FIG. 5 will generally be described with reference to the cochlear implant system 102 of FIGS. 1A-1D. However, as explained elsewhere herein, the hybrid multi-phasic stimulation techniques may be applied in a variety of contexts and may be implemented by a number of different types of implantable medical devices.

FIG. 5 includes a first curve/trace 562 illustrating the current associated with the hybrid multi-phasic stimulation signal 560 at the interface between the implanted electrodes 144 and the recipient's cochlea (e.g., the electrode-tissue interface). Stated differently, curve 562 illustrates the instantaneous current injected or withdrawn from the electrode-tissue interface, over time. FIG. 5 also includes a second curve/trace 564 illustrating the voltage associated with the with the hybrid multi-phasic stimulation signal 560 at the electrode-tissue interface. That is, curve 564 illustrates the instantaneous voltage at the electrode-tissue interface, over time. In FIG. 5, the voltage curve 564 is shown in a simplified form that ignores IR offset.

The hybrid multi-phasic stimulation signal 560 begins with a first current pulse 550 (current pulse) having a first polarity. In this example, the first current pulse 550 is an anodic (+) current pulse and is the portion of the hybrid multi-phasic stimulation signal 560 that evokes a percept from the recipient (i.e., the portion of the signal that depolarizes axons and triggers an action potential). As such, in this example, the anodic current pulse 550 is sometimes referred to herein as a "stimulation pulse" and the hybrid multi-phasic stimulation signal 560 is sometimes referred to herein as an "anodic hybrid multi-phasic stimulation signal."

As shown in FIG. 5, the first current pulse 550 is followed by an Inter Phase Gap (IPG) 551, which is a time period in which no current is delivered to, or withdrawn from, the electrode-tissue interface. In accordance with the hybrid multi-phasic stimulation techniques presented herein, the IPG 551 is followed by a first period 570 of shorting (shorting period) during which all the implantable electrodes 144 are "shorted" together. The shorting period 570 has a time length that is sufficient to withdraw only part of the residual charge from the tissue-electrode interface. That is, as shown in FIG. 5, at the end 571 of the shorting period 570, a residual charge remains at the electrode-tissue interface.

To remove or substantially reduce the residual charge remaining at the electrode-tissue interface, the hybrid multi-phasic stimulation signal 560 comprises a second current pulse 552 (current pulse) having a second polarity. As noted, in the example of FIG. 5, the first current pulse 550 is an anodic pulse. As such, in this example, the second current pulse 552 is a cathodic current pulse (e.g., the stimulator unit 142 is configured to discharge anions (−) into the electrode-tissue interface). Since the second current pulse 552 is the portion of the hybrid multi-phasic stimulation signal 560 that balances residual charge, the second current pulse 552 is sometimes referred to herein as a "discharging pulse."

As noted above, the shorting period 570 is provided between the first current pulse 550 and the second current pulse 552 and removes some of the charge introduced into the electrode-tissue interface by the first current pulse 550. That is, at the beginning of the second current pulse 552, some charge has already been removed from the electrode-tissue interface. As a result, since the second current pulse 552 does not have to discharge all of the charge introduced by the anodic pulse 550, the second pulse 552 has a time length (and/or amplitude) that is less than the first current pulse 550. That is, the first current pulse 550 and the second current pulse 552 are "unbalanced," meaning that the charge discharged by the second current pulse 552 is not the same as the charge introduced by the first current pulse 550. Instead, the charge discharged by the combination of the shorting period 570 and the second current pulse 552 is generally equivalent to the charge introduced by the first current pulse 550. Stated differently, the shorting period 570 and the second current pulse 552 are collectively configured to "balance" the charge at the electrode-tissue interface (e.g., ensure that the residual charge at the electrode-tissue interface is reduced at least to a level such that there is a net average DC current flow below a predetermined threshold).

Since the charge discharged by the second current pulse 552 is not the same as the charge introduced by the first current pulse 550, the second current pulse 552 is sometimes referred to as an "abbreviated" or "condensed" discharging pulse. Similarly, since the charge withdrawn by the shorting period 570 is not the same as the charge introduced by the first current pulse 550, the shorting period 570 is sometimes referred to as an "abbreviated" or "condensed" shorting period.

In the example of FIG. 5, the hybrid multi-phasic stimulation signal 560 also includes a second period of shorting 572 (second shorting period) after the anodic pulse 552. The second shorting period 572 may operate as a safety mechanism to, in certain examples, ensure that the residual charge at the electrode-tissue interface is reduced at least to a level such that there is a net average DC current flow below a predetermined threshold.

The presence of the second shorting period 572 increases the time length of the hybrid multi-phasic stimulation signal 560. As such, it may be advantageous to adaptively eliminate the second shorting period 572. To this end, in certain examples, the cochlear implant system 102 is configured to measure the voltage 564 at the electrode-tissue interface after the second current pulse 552. By performing a plurality of such measurements over time (e.g., during a plurality of different hybrid multi-phasic stimulation signals), the cochlear implant system 102 can adapt future stimulation signals (e.g., adapt the attributes of future discharging pulses) in a manner that ensures future shorting period 570 and the second current pulses 552 can ensure the residual charge at the electrode-tissue interface is reduced at least to a level such that there is a net average DC current flow below a predetermined threshold, without the need for the second shorting period.

In the example of FIG. 5, the shorting period 570 occurs between the anodic pulse 550 and the cathodic pulse 552. As such, in this example, the shorting period 570 is sometimes referred to as an "intra-pulse" shorting period. In other embodiments, the cathodic pulse 552 could precede the shorting period 570 (e.g., similar to signal 460(C) of FIG. 4C).

FIG. 5 include a curve 553 illustrating removal of the charge in accordance with standard monophasic stimulation (e.g., without the abbreviated discharging pulse 552, such as monophasic stimulation signal 349 of FIG. 3). As can be seen from curve 553, the hybrid multi-phasic stimulation signal 560 has a total time length 573 that is shorter than a time length 575 of a standard monophasic stimulation signal (e.g., monophasic stimulation signal 349).

FIG. 5 has been primarily described with reference to a time length difference between the anodic pulse 550 and the cathodic pulse 552 that makes the two current pulses unbalanced. However, it is to be appreciated that the charge imbalance between the cathodic pulse 550 and the anodic pulse 552 may be a result of other signal attributes, such as different amplitudes, a combination of different amplitudes and different time lengths, etc.

In the example of FIG. 5, cochlear implant system 102 generates the anodic current pulse 550 to trigger action potentials in the recipient's auditory neurons (e.g., based on received sound signals). After the IPG 551, the cochlear implant system 102 initiates the initial shorting period 570 to remove an amount of the charge at the electrode-tissue interface. Once the voltage 564 drops to a predetermined level (e.g., approximately half of its peak value), the cochlear implant system 102 generates the abbreviated (low energy) discharging pulse 552 to accelerate the removal of the remaining stored charge.

Although the abbreviated discharging 552 does require some consume some power from the cochlear implant system 102, the power consumed is significantly less than a full cathodic pulse used in a typical biphasic stimulation strategy. As noted, the energy injected during the anodic pulse 550 has to be extracted by the combination of the shorting period 570 and the cathodic pulse 552. For example, if the initial shorting period 570 were to reduce the voltage across the electrode-tissue interface (acting as a capacitor) to a half of the peak value, then the energy required to fully discharge the electrode-tissue interface is only one quarter of the energy required by the anodic pulse in typical biphasic stimulation.

As noted, at the end of the hybrid multi-phasic stimulation signal 560, the remaining/residual charge must be at least at level such that there is a net average DC current flow below a predetermined threshold (e.g., approximately less than 100 nA). As such, the charge to be injected with the cathodic pulse 552 must be coordinated with the charge withdrawn via the shorting period 570 as any error (positive or negative) in the cathodic charge injection will need to be dissipated in the second shorting period 572. Therefore, a larger error in the cathodic pulse 552 requires a longer second shorting period 572, which in turn makes the hybrid multi-phasic stimulation signal 560 less suited for higher stimulation rate strategies. Similarly, as noted above, the second shorting period 572 can be totally avoided if the cathodic charge injection of the discharging pulse 552 is accurate enough to ensure an average DC current below the predetermined threshold (e.g., less than 100 nA). The charge that needs to be withdrawn via the cathodic pulse 552, and hence the parameters (e.g., amplitude, time length, etc.) can be determined as described above with reference to the embodiments of FIGS. 4A and 4B.

Figure 6:
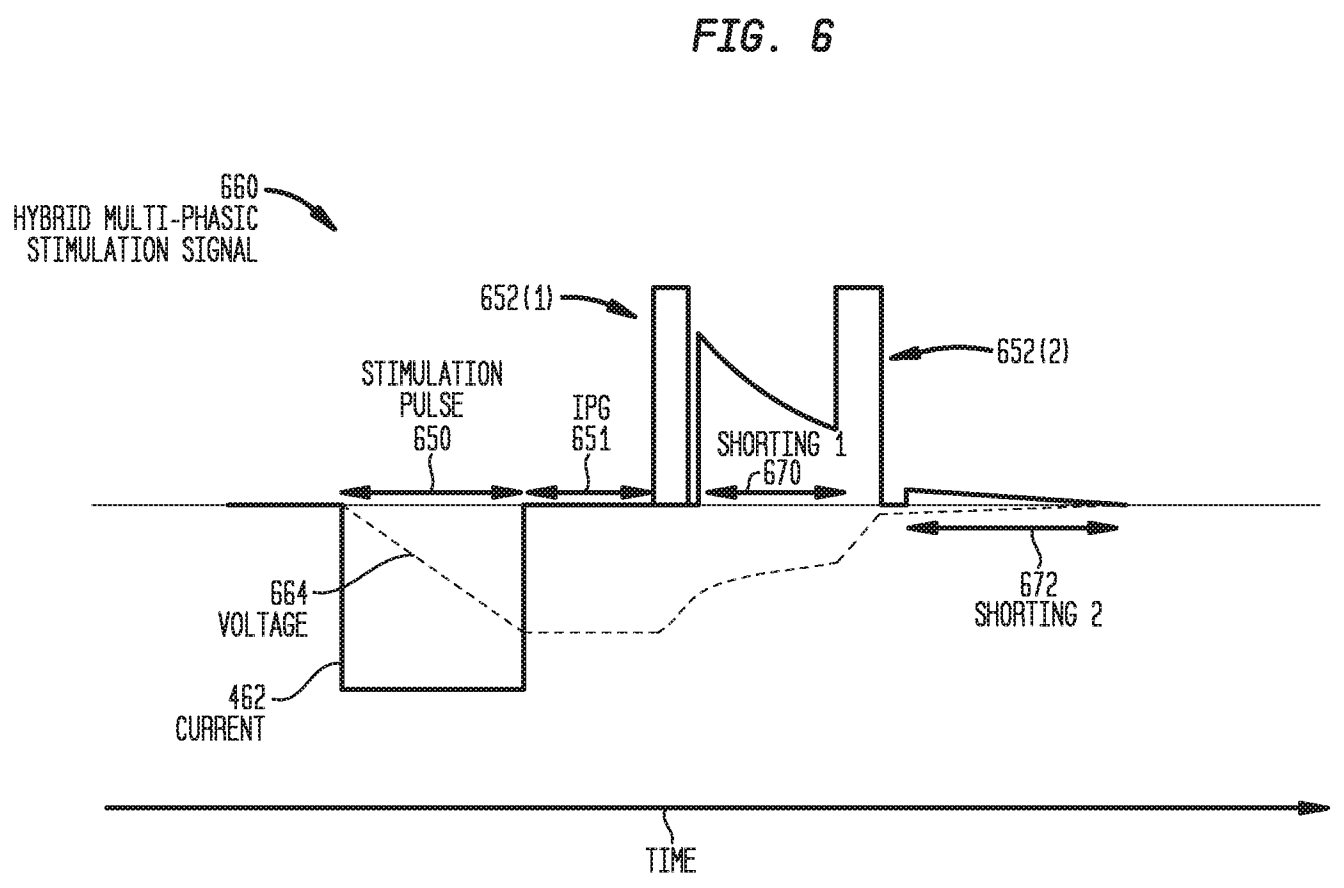

FIG. 6 illustrates another example hybrid multi-phasic stimulation signal 660 in accordance with certain embodiments presented herein. The hybrid multi-phasic stimulation signal 660 is generally a hybrid biphasic stimulation signal that comprises two discharging pulses, rather than a single discharging pulse as in the examples of FIGS. 4A, 4B, and 5.

More specifically, FIG. 6 includes a first curve/trace 662 illustrating the current associated with the hybrid multi-phasic stimulation signal 660 at the interface between the implanted electrodes 144 and the recipient's cochlea (e.g., the electrode-tissue interface). Stated differently, curve 662 illustrates the instantaneous current injected or withdrawn from the electrode-tissue interface, over time. FIG. 6 also include a second curve/trace 664 illustrating the voltage associated with the hybrid multi-phasic stimulation signal 660 at the electrode-tissue interface. That is, curve 664 illustrates the instantaneous voltage at the electrode-tissue interface, over time. In FIG. 6, the voltage curve 664 is shown in a simplified form that ignores IR offset.

The hybrid multi-phasic stimulation signal 660 begins with a first current pulse 650 (current pulse) having a first polarity. In this example, the first current pulse 650 is a cathodic (−) current pulse. The first current pulse 650 is the portion of the hybrid multi-phasic stimulation signal 660 that evokes a percept from the recipient. As such, the first current pulse 650 is sometimes referred to herein as a "stimulation pulse" and the hybrid multi-phasic stimulation signal 660 is sometimes referred to herein as a "cathodic hybrid multi-phasic stimulation signal."

As shown in FIG. 6, the first current pulse 650 is followed by an Inter Phase Gap (IPG) 651, which is a time period in which no current is delivered to, or withdrawn from, the electrode-tissue interface. In accordance with the hybrid multi-phasic stimulation techniques presented herein, the IPG 651 is followed by a second current pulse 652(1), which in turn is followed by a first period 670 of shorting (shorting period) during which all the implantable electrodes 144 are shorted together. The shorting period 670 is followed by a third current pulse 652(2). The second current pulse 652(1), shorting period 670, and third current pulse 652(2) are collectively configured to "balance" the first current pulse 650. That is, the second current pulse 652(1), shorting period 670, and third current pulse 652(2) function to remove or substantially reduce the residual charge remaining at the electrode-tissue interface.

As noted, in the example of FIG. 6, the first current pulse 650 is a cathodic pulse. As such, in this example, the second current pulse 652(1) and the third current pulse 652(2) are each anodic current pulses. The second current pulse 652(1) and the third current pulse 652(2) collectively comprise the portion of the hybrid multi-phasic stimulation signal 660 that discharges residual charge and, as such, are sometimes referred to herein as "discharging pulses."

In general, the example of FIG. 6 is similar to that of FIGS. 4A and 4B, except that the single discharging pulse used in the examples of FIGS. 4A and 4B is split into two discharging pulses that are separated by the shorting period 670, which has a time length that is sufficient to withdraw only part of the residual charge from the tissue-electrode interface. The second current pulse 652(1) is a brief pulse configured to reduce the peak current at the beginning of the shorting period 670.

As noted above, the shorting period 670 is provided between the second current pulse 652(1) and the third current pulse 652(2) and removes some of the charge introduced into the electrode-tissue interface by the cathodic pulse 650. As a result, since the second current pulse 652(1) and the third current pulse 652(2) do not have to discharge all of the charge introduced by the cathodic pulse 650, the second current pulse 652(1) and the third current pulse 652(2) collectively have a time length (and/or amplitude) that is less than the cathodic pulse 650. That is, the cathodic pulse 650 and the combination of the two anodic pulses 652(1) and 652(2) are "unbalanced," meaning that the charge discharged by the combination of the two anodic pulses 652(1) and 652(2) is not the same as the charge introduced by the cathodic pulse 650. Instead, the charge discharged by the combination of the shorting period 670 and the two anodic pulses 652(1) and 652(2) is generally equivalent to the charge introduced by the cathodic pulse 650. Stated differently, the shorting period 670 and the two anodic pulses 652(1) and 652(2) are collectively configured to "balance" the charge at the electrode-tissue interface (e.g., ensure that the residual charge at the electrode-tissue interface is reduced at least to a level such that there is a net average DC current flow below a predetermined threshold).

Since the charge discharged by the two anodic pulses 652(1) and 652(2) is not the same as the charge introduced by the cathodic pulse 650, the two anodic pulses 652(1) and 652(2) are sometimes referred to as "abbreviated" or "condensed" discharging pulses. Similarly, since the charge withdrawn by the shorting period 670 is not the same as the charge introduced by the cathodic pulse 650, the shorting period 670 is sometimes referred to as an "abbreviated" or "condensed" shorting period.

In the example of FIG. 6, the hybrid multi-phasic stimulation signal 660 also includes a second period of shorting 672 (second shorting period) after the anodic pulse 652. The second shorting period 672. However, as noted elsewhere herein, the shorting period 672 may, in certain embodiments, be omitted or adaptively eliminated.

In accordance with the techniques presented herein, the amplitude of the current during shorting is not controlled by the implantable medical device and, instead, the current is the residual voltage divided by the tissue impedance. As such, the current may be higher than desirable at the start of the shorting period. FIG. 6 illustrates an example in which the peak current can be reduced through the use of a small/brief discharging pulse (where the current is controlled) prior to the shorting period (e.g., signal 660 has reduced power requirements, shorter time, and a limit to the initial peak shorting current).

FIGS. 4A, 4B, 5, and 6 have been described with reference to hybrid multi-phasic stimulation signals that are generally biphasic in nature. It is to be appreciated that hybrid multi-phasic stimulation signals may include different numbers of current pulses, such as triphasic stimulation signals. Triphasic stimulation, for example, three (3) current pulses with alternating polarity (e.g., either a cathodic-anodic-cathodic pulse sequence or an anodic-cathodic-anodic pulse sequence). In a conventional triphasic stimulation signal, the current injected by the second current pulse generally "balances" the current injected by the first and third current pulses. That is, in general, the charge injected by the second current pulse is approximately equal to the current injected by the combination of the first and third current pulses, but with an opposite polarity. In certain conventional triphasic stimulation signals, the first and third pulses each inject substantially the same amount of charge into the electrode-tissue interface. Due to the charge balancing via equal and opposite polarities, conventional triphasic stimulation may consume substantial amounts of power.

Figure 7:
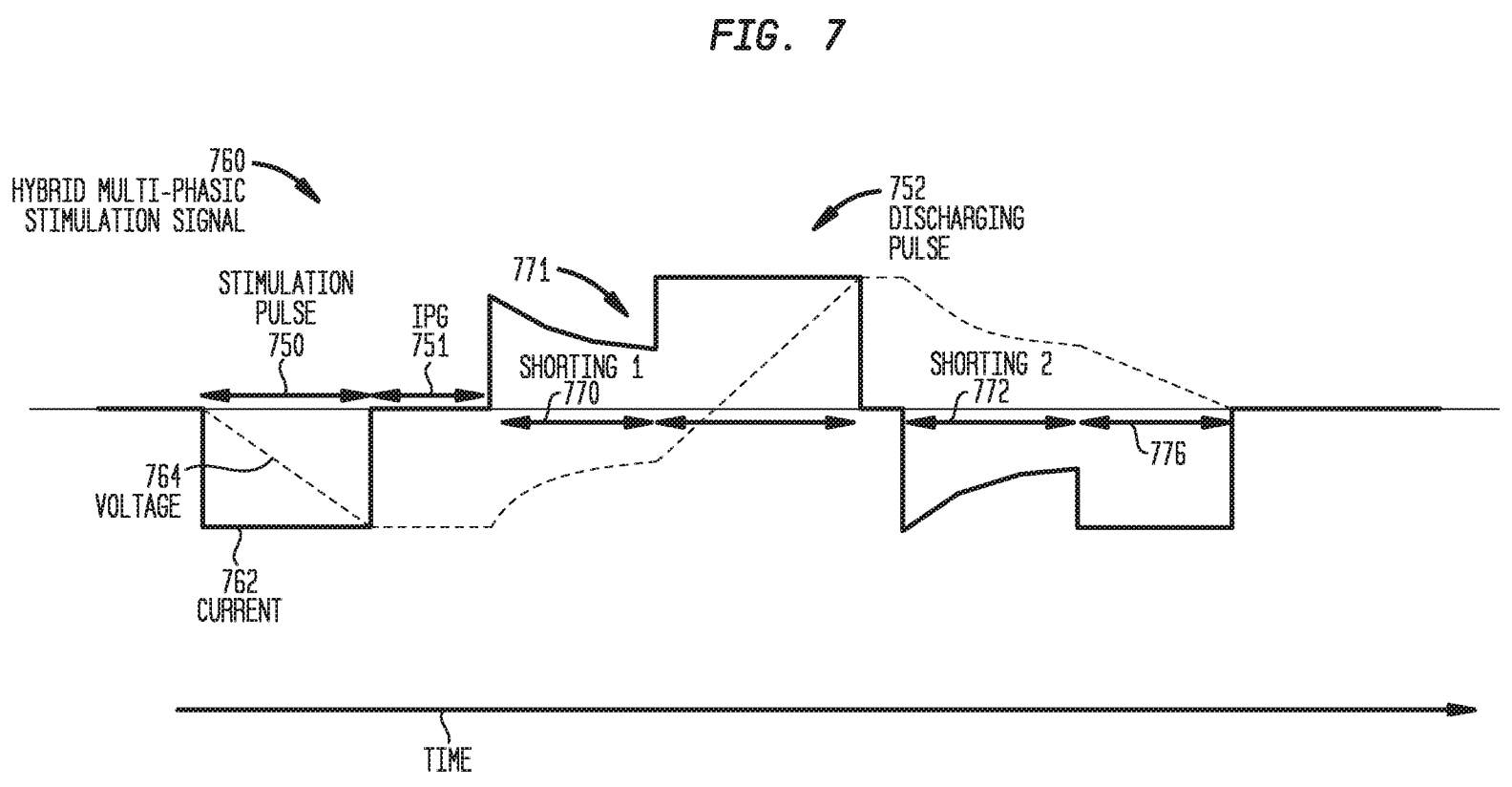

FIG. 7 illustrates an example hybrid multi-phasic stimulation signal 760 that is generally triphasic in nature, but which consumes less power than a standard/conventional triphasic stimulation signal. More specifically, FIG. 7 includes a first curve/trace 762 illustrating the current associated with the hybrid multi-phasic stimulation signal 760 at the interface between the implanted electrodes 144 and the recipient's cochlea (e.g., the electrode-tissue interface). Stated differently, curve 762 illustrates the instantaneous current injected or withdrawn from the electrode-tissue interface, over time. FIG. 7 also includes a second curve/trace 764 illustrating the voltage associated with the with the hybrid multi-phasic stimulation signal 760 at the electrode-tissue interface. That is, curve 764 illustrates the instantaneous voltage at the electrode-tissue interface, over time. In FIG. 7, the voltage curve 764 is shown in a simplified form that ignores IR offset.

The hybrid multi-phasic stimulation signal 760 begins with a first current pulse 750 (current pulse) having a first polarity and ends with a third current pulse 776 also having the same first polarity (either both cathodic or both anodic). Between the first pulse 750 and the third current pulse 776 is a second current pulse 752 having the opposite polarity. That is, the first and third current pulses have the same polarity, and the second current pulse has the opposite polarity.

In the example of FIG. 7, the first current pulse 750 and the third current pulse 776 are both cathodic (−) current pulses and the second current pulse 752 is an anodic (+) current pulse. However, as noted elsewhere herein, in alternative embodiments the polarities may be inverted (e.g., the first and third current pulses may be anodic and the second phase pulse may be cathodic).

As shown in FIG. 7, the cathodic current pulse 750 is followed by an Inter Phase Gap (IPG) 751, which is a time period in which no current is delivered to, or withdrawn from, the electrode-tissue interface. In accordance with the hybrid multi-phasic stimulation techniques presented herein, the IPG 751 is followed by a first period 770 of shorting (shorting period) during which all the implantable electrodes 144 are shorted together.

The shorting period 770 is followed by the second current pulse 752 which, as noted above, has an opposing polarity to the first current pulse 750. The second current pulse 752 is followed by another period of shorting 772 (shorting period) during which during which all the implantable electrodes 144 are shorted together. The shorting period 772 is followed by the third current pulse 776 which, as noted above, has the same polarity to the first current pulse 750.

Each of the shorting periods 770 and 772 are configured to remove some of the charge from the tissue. In particular, shorting period 770 removes some of the charge introduced into the electrode-tissue interface by the cathodic pulse 750, while the shorting period 772 removes some of the charge introduced into the electrode-tissue interface by the anodic pulse 752. Due to the use of the shorting periods 770 and 772, each of the anodic pulse 752 and the cathodic pulse 776 can have a time length (and/or amplitude) that is less than the second and third stimulation pulses in conventional triphasic stimulation signals. That is, the pulses 750, 752, and 776 are generally "unbalanced," meaning that the charge discharged by the anodic pulse 752 is not the same as the charge introduced by the cathodic pulses 750 and 776.

Instead, the charge discharged by the combination of the shorting period 770 and the anodic pulse 752 is generally equivalent to the charge introduced by the cathodic pulse 750, cathodic pulse 776, and the current withdrawn via the shorting period 772. Stated differently, the shorting period 770 and the anodic pulse 752 are collectively configured to "balance" the charge at the electrode-tissue interface (e.g., ensure that the residual charge at the electrode-tissue interface is reduced at least to a level such that there is a net average DC current flow below a predetermined threshold).

FIG. 7 have been primarily described with reference to a time length difference between the cathodic pulse 750, cathodic pulse 776, and the anodic pulse 752 that makes the current pulses unbalanced. However, it is to be appreciated that the charge imbalance between the cathodic pulse 750, cathodic pulse 776, and the anodic pulse 752 may be a result of other signal attributes, such as different amplitudes, different amplitudes and different time lengths, etc.

As noted elsewhere herein, reference to "shorting" of implantable electrodes means that all of the electrodes are connected to a same low impedance (e.g., connected together internally within the implantable medical device). Since the electrodes are all connected to the same low impedance, the shorting, if enabled for a sufficient period of time, dissipates any charge at the electrode-tissue interface, which results in lower or zero potential. That is, the shorting of the electrodes withdraws residual charge from the electrode-tissue interface (e.g., brings all of the electrodes to the same potential, if a shorting period is sufficiently long).

Figure 8:
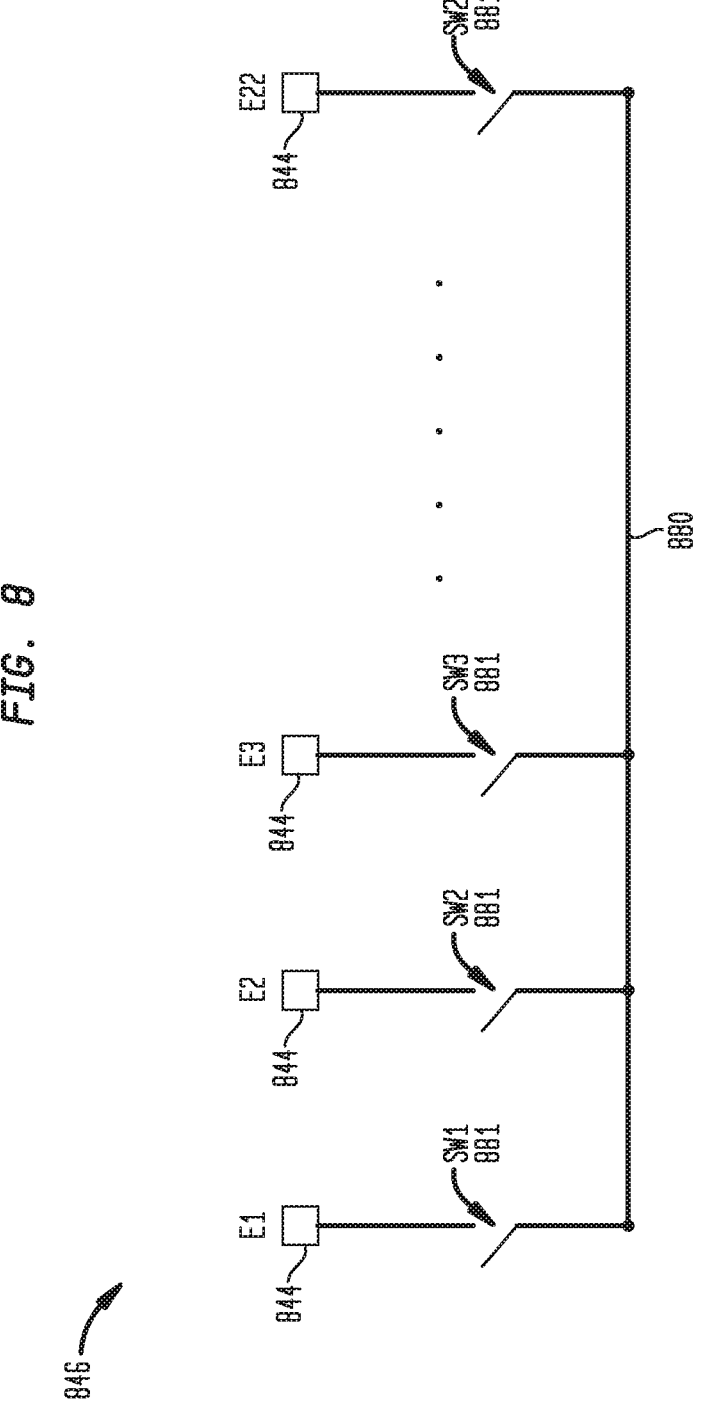
FIG. 8 is a schematic diagram illustrating electrode shorting, in accordance with certain embodiments presented herein.

FIG. 8 illustrates an example embodiment arrangement for shorting a plurality of electrodes. In particular, shown in FIG. 8 is a plurality of electrodes 844 forming an electrode or contact array 846. Each of the electrodes 844 is selectively electrically connectable to a common point 880 via low impedance path comprising a corresponding switch 881. The switches 881 are controlled by the implantable medical device to selectively connect all of the electrodes together, via the low impedance path, to the common point 880 (e.g., dissipates any charge at the electrode-tissue interface). That is, during shorting, all of the switches 881 are closed, thereby forming a low impedance path (short) between all electrodes.

As noted, in the arrangement of FIG. 8, the electrodes 844 are each connected to the same common point 880 via a corresponding switch 881. However, in the example of FIG. 8, when the shorting begins, the implantable medical device is unable to control of the amount of current that flows from the electrodes 844 to the common point 880. That is, as noted, the electrode-tissue interface is capacitive and, when a charge is present, there is a voltage present. The voltage divided by the resistance of the system determines the current that will flow when the shorting begins (e.g., amount of current is controlled by the amount of charge left at that electrode-tissue interface and the impedance of the system, including that of the tissue, wires, etc.). If the resistance of the system is too low, a large initial peak shorting current could be present, where such a large current could, for example, result in an undesirable second percept. Therefore, in accordance with certain embodiments presented herein, the start of the shorting period could include a controllable impedance to limit the initial shorting current, potentially without requiring any power to be supplied by the implantable medical device.

Figure 9:
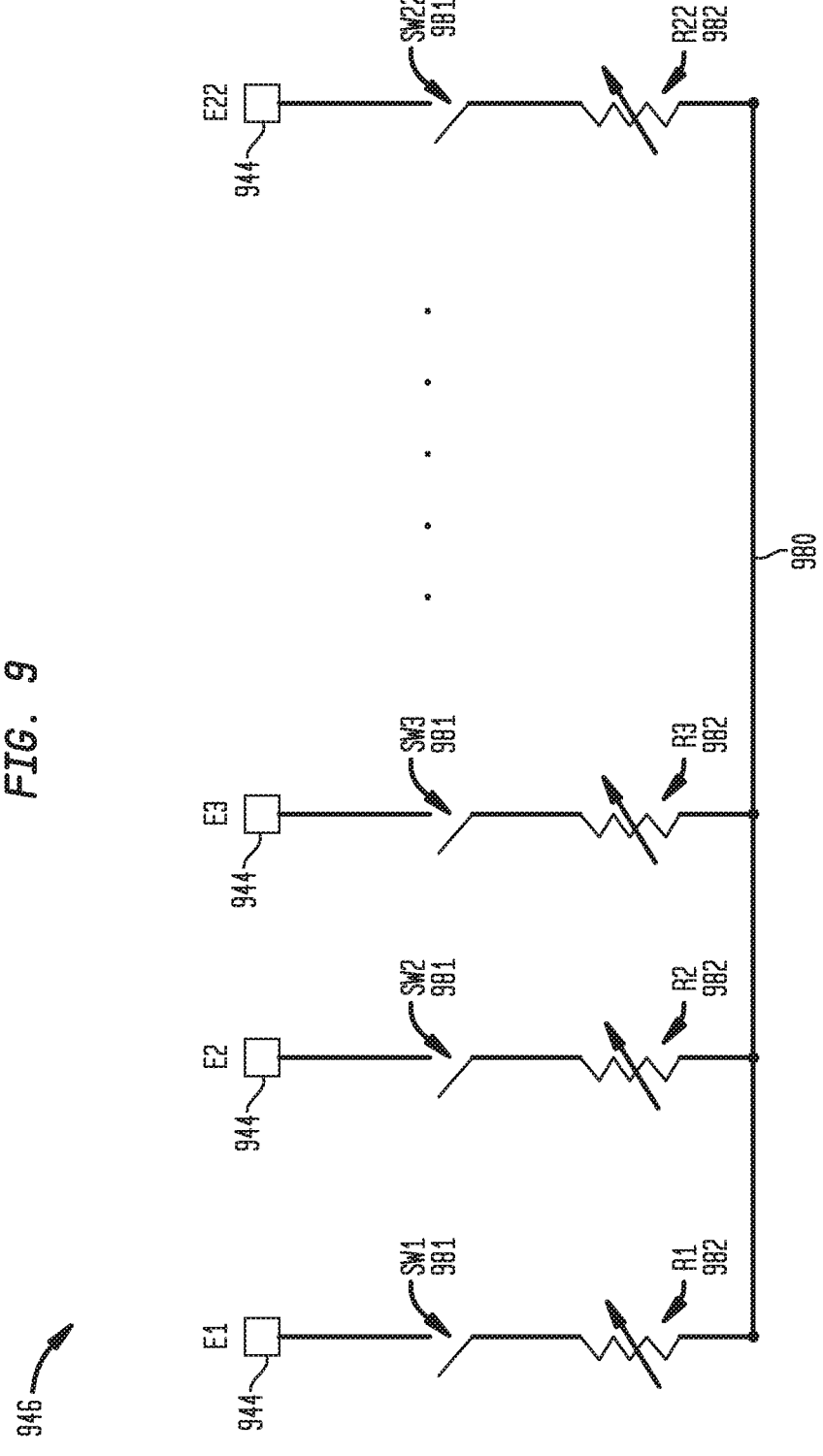
FIG. 9 is another schematic diagram illustrating electrode shorting, in accordance with certain embodiments presented herein.

More specifically, shown in FIG. 9 is a plurality of electrodes 944 forming an electrode or contact array 946. Each of the electrodes 944 is selectively electrically connectable to a common point 980 via a low impedance path that includes a corresponding switch 981 and a corresponding variable resistor 982. The switches 981, and the variable resistors 982, are controlled by the implantable medical device to selectively connect all of the electrodes to the common point 980 (e.g., dissipates any charge at the electrode-tissue interface). However, in contrast to the embodiment of FIG. 8, the addition of the variable resistors 982 enables the implantable medical device to control (e.g., limit) the initial shorting current to a predetermined or dynamically determined (e.g., lower) value.

In addition, during shorting, the voltage at the electrode-tissue interface will decrease. As such, in certain embodiments, the resistance values of the variable resistors 982 can also be dynamically/adaptively decreased to minimize the time needed to remove the charge from the electrodes (e.g., the resistance values of the variable resistors 982 change over time in relation to the voltage at the electrode-tissue interface).

Figure 10:
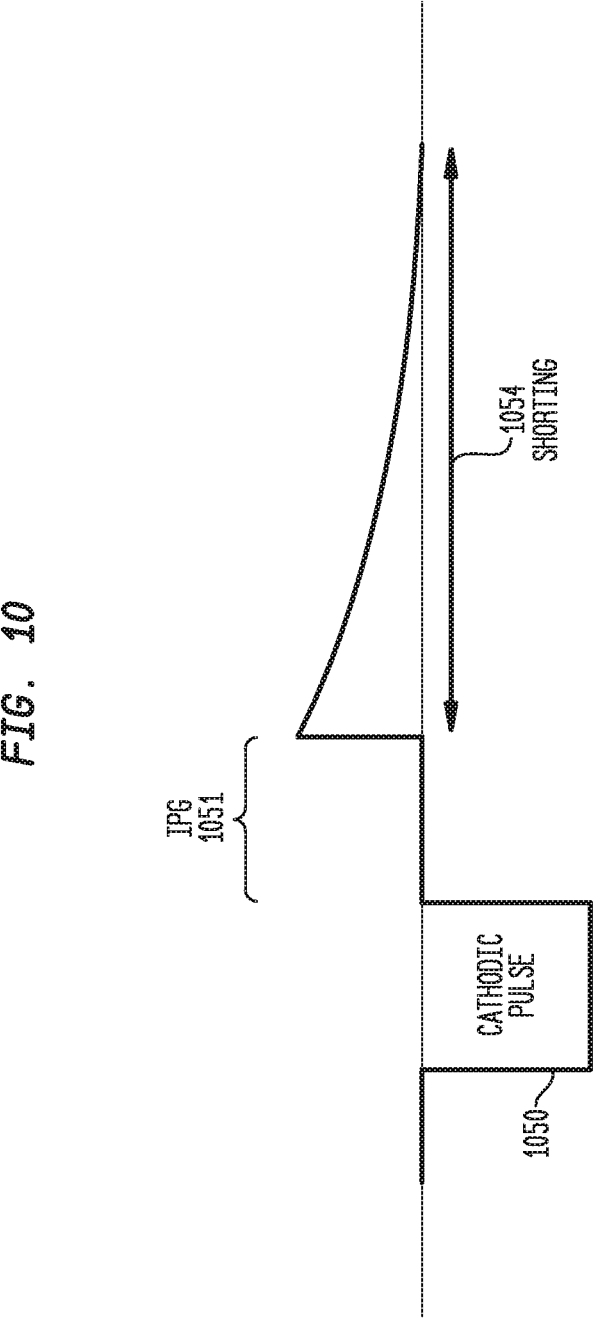
FIG. 10 is a schematic diagram illustrating an example hybrid monophasic stimulation signal, in accordance with certain embodiments presented herein.

FIG. 10 illustrates a hybrid monophasic pulse 1060, in accordance with embodiments presented herein. In the example of FIG. 10, the hybrid monophasic pulse 1060 comprises a single current pulse 1050 (either cathodic or anodic pulse) followed by a period of shorting 1054 (shorting period) to balance the charge. In the example of FIG. 10, an IPG 1051 is provided between the current pulse 1050 and the shorting period 1054. Adding the IPG 1051 makes the hybrid monophasic pulse 1060 more effective than conventional monophasic pulses where, for the same level of current and charge, increasing the IPG 1051 will cause the resulting percept to increase. Stated differently, the same percept can be produced by lowering the current and increasing the IPG 1051, thereby saving power. In general, the tradeoff is stimulation duration and therefore maximum stimulation rate.

Embodiments presented herein have been primarily described with reference to an example auditory prosthesis system, namely a cochlear implant system. However, as noted above, it is to be appreciated that the techniques presented herein may be implemented by a variety of other types of implantable medical devices (or systems that include other types of implantable medical devices) that provide a wide range of therapeutic benefits to recipients, patients, or other users. For example, the techniques presented herein may be implemented by other auditory prostheses, such as acoustic hearing aids, middle ear auditory prostheses, bone conduction devices, direct acoustic stimulators, electro-acoustic prostheses, other electrically simulating auditory prostheses (e.g., auditory brain stimulators), etc. The techniques presented herein may also be implemented by tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

FIG. 11 illustrates an example vestibular stimulator system 1102 in accordance with embodiments presented herein. In this example, the vestibular stimulator system 1102 comprises an implantable component (vestibular stimulator) 1112 and an external device/component 1104 (e.g., external processing device, battery charger, remote control, etc.).

The vestibular stimulator 1112 comprises an implant body (main module) 1134, a lead region 1136, and a stimulating assembly 1116, all configured to be implanted under the skin/tissue (tissue) 1115 of the recipient. The implant body 1134 generally comprises a hermetically-sealed housing 1138 in which RF interface circuitry, one or more rechargeable batteries, one or more processors, and a stimulator unit are disposed. The implant body 134 also includes an internal/implantable coil 1114 that is generally external to the housing 1138, but which is connected to the transceiver via a hermetic feedthrough (not shown).

The stimulating assembly 1116 comprises a plurality of electrodes 1144 disposed in a carrier member (e.g., a flexible silicone body). In this specific example, the stimulating assembly 1116 comprises three (3) stimulation electrodes, referred to as stimulation electrodes 1144(1), 1144(2), and 1144(3). The stimulation electrodes 1144(1), 1144(2), and 1144(3) function as an electrical interface for delivery of electrical stimulation signals to the recipient's vestibular system. In accordance with embodiments presented herein, the vestibular nerve stimulator 1102 is configured to stimulate the recipient's vestibular system using hybrid multiphasic stimulation signals or hybrid monophasic stimulation signals, such as the signals described above with reference to FIGS. 4A, 4B, 5, 6, 7, and 10. That is, the vestibular nerve stimulator system 1102 is configured to generate and deliver hybrid multi-phasic stimulation signals or hybrid monophasic stimulation signals to receive via one or more of the stimulation electrodes 1144(1), 1144(2), and 1144(3).

The stimulating assembly 1116 is configured such that a surgeon can implant the stimulating assembly adjacent the recipient's otolith organs via, for example, the recipient's oval window. It is to be appreciated that this specific embodiment with three stimulation electrodes is merely illustrative and that the techniques presented herein may be used with stimulating assemblies having different numbers of stimulation electrodes, stimulating assemblies having different lengths, etc.

FIG. 12 is a flowchart of a method 1290 in accordance with embodiments presented herein. Method 1290 begins at 1292 where an implantable medical device delivers via at least one of a plurality of implantable electrodes, a stimulation current pulse to inject charge into tissue of a recipient of the implantable medical device. At 1294, the implantable medical device shorts the at least one of the plurality of implantable electrodes with one or more other of the plurality of implantable electrodes to remove a first portion of the charge injected into the tissue by the stimulation current pulse. At 1296, the implantable medical device delivers at least one discharging current pulse to the tissue of the recipient to remove a second portion of the charge injected into the tissue by the stimulation current pulse.

Figure 13:
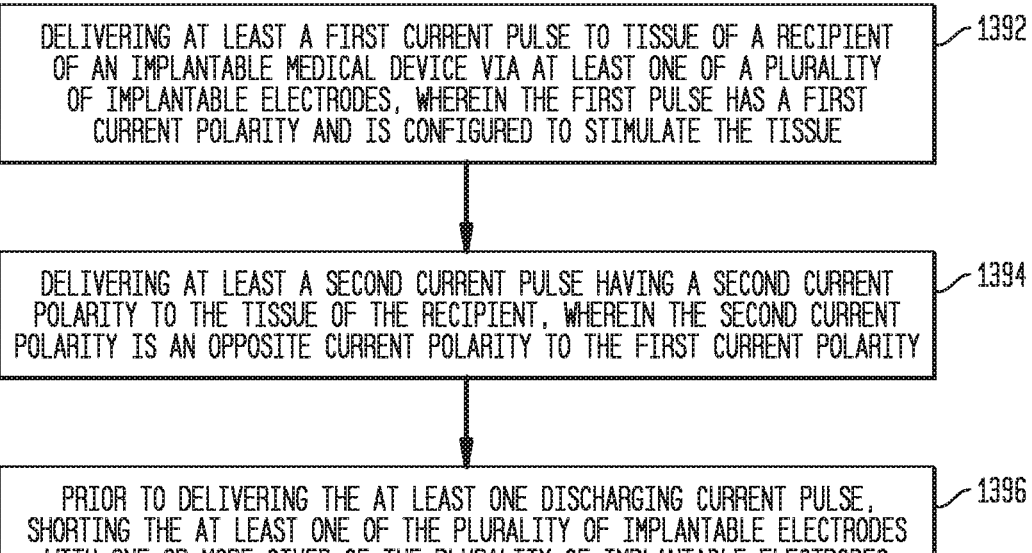
FIG. 13 is a flowchart of another method, in accordance with certain embodiments presented herein.

FIG. 13 is a flowchart of a method 1390 in accordance with embodiments presented herein. Method 1390 begins at 1392 where an implantable medical device delivers at least a first current pulse to tissue of a recipient of an implantable medical device via at least one of a plurality of implantable electrodes, wherein the first pulse has a first current polarity and is configured to stimulate the tissue. At 1394, the implantable medical device delivers at least a second current pulse having a second current polarity to the tissue of the recipient, wherein the second current polarity is an opposite current polarity to the first current polarity. At 1396, prior to delivering the at least one discharging current pulse, the implantable medical device shorts the at least one of the plurality of implantable electrodes with one or more other of the plurality of implantable electrodes.

FIG. 14 is a flowchart of a method 1490 in accordance with embodiments presented herein. Method 1490 begins at 1492 where an implantable medical device delivers at least one stimulation current pulse to stimulate tissue of a recipient of an implantable medical device, wherein the at least one stimulation current pulse injects charge into the tissue of the recipient. At 1494, the implantable medical device removes the charge injected into the tissue by the least one stimulation current pulse through a combination of at least one discharging current pulse and a period of electrode shorting that precedes the at least one discharging current pulse.

It is to be appreciated that the embodiments presented herein are not mutually exclusive and that the various embodiments may be combined with another in any of a number of different manners.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
injecting a charge into tissue of a recipient of an implantable medical device by delivering, via at least one of a plurality of implantable electrodes of the implantable medical device, a stimulation current pulse;
removing a first portion of the charge injected into the tissue by the stimulation current pulse by shorting the at least one of the plurality of implantable electrodes with one or more other of the plurality of implantable electrodes; and
removing a second portion of the charge injected into the tissue by the stimulation current pulse by delivering at least one discharging current pulse to the tissue of the recipient after shorting the at least one of the plurality of implantable electrodes with the one or more other of the plurality of implantable electrodes.

2. The method of claim 1, comprising delivering a first discharging current pulse to the tissue prior to shorting the at least one of the plurality of implantable electrodes with the one or more other of the plurality of implantable electrodes, wherein delivering the at least one discharging current pulse to the tissue comprises delivering a second discharging current pulse to the tissue after shorting the at least one of the plurality of implantable electrodes with the one or more other of the plurality of implantable electrodes.

3. The method of claim 1, wherein the stimulation current pulse has a first current polarity and the at least one discharging current pulse has second current polarity, wherein the second current polarity is an opposite current polarity to the first current polarity.

4. The method of claim 1, wherein removing the first portion of the charge injected into the tissue by the stimulation current pulse by shorting the at least one of the plurality of implantable electrodes with the one or more other of the plurality of implantable electrodes comprises:
shorting all of the plurality of implantable electrodes together to a common point of the implantable medical device via one or more low impedance paths.

5. The method of claim 1, wherein removing the first portion of the charge injected into the tissue by the stimulation current pulse by shorting the at least one of the plurality of implantable electrodes with the one or more other of the plurality of implantable electrodes comprises:
during the shorting, controlling a flow of current from the tissue to a common point of the implantable medical device via one or more low impedance paths.

6. The method of claim 5, wherein the at least one of the plurality of implantable electrodes and the one or more other of the plurality of implantable electrodes are each connected to the common point via a corresponding one of a plurality of switches and corresponding one of a plurality of resistor elements.

7. The method of claim 6, wherein the plurality of resistor elements comprise a plurality of variable resistor elements, and wherein controlling the flow of current from the tissue to the common point of the implantable medical device comprises:
adjusting, over time, a resistance value of one or more of the plurality of variable resistor elements.

8. The method of claim 1, wherein the stimulation current pulse and the at least one discharging current pulse are unbalanced.

9. The method of claim 1, further comprising:
determining one or more attributes of the at least one discharging current pulse controlling the second portion of the charge removed from the tissue based, at least in part, on impedances of the plurality of implantable electrodes.

10. The method of claim 1, further comprising:
measuring an instantaneous voltage at the tissue after the shorting of the at least one of the plurality of implantable electrodes with the one or more other of the plurality of implantable electrodes; and
dynamically determining one or more attributes of the at least one discharging current pulse controlling the second portion of the charge removed from the tissue based, at least in part, on the instantaneous voltage at the tissue after the shorting of the at least one of the plurality of implantable electrodes with the one or more other of the plurality of implantable electrodes.

11. The method of claim 10, further comprising:
measuring an instantaneous voltage at the tissue after the stimulation current pulse is injected into the tissue; and
dynamically determining the one or more attributes of the at least one discharging current pulse controlling the second portion of the charge removed from the tissue based, at least in part, on the instantaneous voltage at the tissue after the stimulation current pulse is injected into the tissue and the instantaneous voltage at the tissue after the shorting of the at least one of the plurality of implantable electrodes with the one or more other of the plurality of implantable electrodes.

12. The method of claim 1, further comprising:
providing an Inter Phase Gap from the stimulation current pulse to the shorting of the at least one of the plurality of implantable electrodes with the one or more other of the plurality of implantable electrodes.

13. An implantable medical device, comprising:
a stimulation subsystem configured to generate a stimulation current pulse;
a plurality of implantable electrodes configured to be implanted adjacent to tissue of a recipient of the implantable medical device, wherein at least one of the plurality of implantable electrodes is configured to deliver the stimulation current pulse to inject charge into the tissue of the recipient; and
a plurality of switches configured to short the at least one of the plurality of implantable electrodes with one or more other of the plurality of implantable electrodes to remove a first portion of the charge injected into the tissue by the stimulation current pulse,
wherein the stimulation subsystem is configured to generate at least one discharging current pulse for delivery to the tissue of the recipient to remove a second portion of the charge injected into the tissue by the stimulation current pulse, wherein the stimulation subsystem is configured to close one or more of the plurality of switches to short the at least one of the plurality of implantable electrodes with the one or more other of the plurality of implantable electrodes after generating the stimulation current pulse and provide an Inter Phase Gap from the stimulation current pulse to shorting of the at least one of the plurality of implantable electrodes, and wherein no current is delivered to or withdrawn from the plurality of implantable electrodes during the Inter Phase Gap.

14. The implantable medical device of claim 13, wherein the at least one discharging current pulse comprises a plurality of discharging current pulses collectively configured to remove the second portion of the charge injected into the tissue by the stimulation current pulse.

15. The implantable medical device of claim 13, wherein the stimulation current pulse has a first current polarity and the at least one discharging current pulse has a second current polarity, wherein the second current polarity is an opposite current polarity to the first current polarity.

16. The implantable medical device of claim 13, wherein the stimulation subsystem is configured to close the one or more of the plurality of switches to short the at least one of the plurality of implantable electrodes with the one or more other of the plurality of implantable electrodes to a common point.

17. A method, comprising:

delivering, via at least one of a plurality of implantable electrodes of an implantable medical device, a stimulation current pulse to inject charge into tissue of a recipient of the implantable medical device;

shorting the at least one of the plurality of implantable electrodes with one or more other of the plurality of implantable electrodes to remove a first portion of the charge injected into the tissue by the stimulation current pulse;

measuring an instantaneous voltage at the tissue after the shorting of the at least one of the plurality of implantable electrodes with the one or more other of the plurality of implantable electrodes;

dynamically determining one or more attributes of at least one discharging current pulse controlling a second portion of the charge removed from the tissue based, at least in part, on the instantaneous voltage at the tissue after the shorting of the at least one of the plurality of implantable electrodes with the one or more other of the plurality of implantable electrodes; and delivering the at least one discharging current pulse to the tissue of the recipient to remove the second portion of the charge injected into the tissue by the stimulation current pulse.

18. The method of claim 17, comprising providing an Inter Phase Gap from the stimulation current pulse to the shorting of the at least one of the plurality of implantable electrodes with the one or more other of the plurality of implantable electrodes, wherein no current is delivered to or withdrawn from the plurality of implantable electrodes during the Inter Phase Gap.

19. The method of claim 17, wherein the stimulation current pulse and the at least one discharging current pulse are unbalanced and of opposite polarity.

* * * * *